(12) United States Patent
Detmer et al.

(10) Patent No.: US 11,961,412 B2
(45) Date of Patent: Apr. 16, 2024

(54) INFANT FEEDING REINFORCEMENT SYSTEM

(71) Applicant: INNOVATIVE THERAPEUTIX, INC., Louisville, KY (US)

(72) Inventors: Michael Detmer, Louisville, KY (US); Rebekah Gossom, Louisville, KY (US)

(73) Assignee: INNOVATIVE THERAPEUTIX, INC., Louisville, KY (US)

( * ) Notice: Subject to any disclaimer, the term of this patent is extended or adjusted under 35 U.S.C. 154(b) by 0 days.

(21) Appl. No.: 17/800,396

(22) PCT Filed: Feb. 26, 2021

(86) PCT No.: PCT/US2021/019935
§ 371 (c)(1),
(2) Date: Aug. 17, 2022

(87) PCT Pub. No.: WO2021/174020
PCT Pub. Date: Sep. 2, 2021

(65) Prior Publication Data
US 2023/0085563 A1    Mar. 16, 2023

Related U.S. Application Data

(60) Provisional application No. 62/982,067, filed on Feb. 27, 2020.

(51) Int. Cl.
*G09B 19/00* (2006.01)
*A61J 11/00* (2006.01)
(Continued)

(52) U.S. Cl.
CPC ....... *G09B 19/0092* (2013.01); *A61J 11/0075* (2013.01); *H04R 1/028* (2013.01); *H04R 3/00* (2013.01); *A61J 2200/70* (2013.01)

(58) Field of Classification Search
CPC .. G09B 19/0092; A61J 11/0075; H04R 1/028; H04R 3/00
See application file for complete search history.

(56) References Cited

U.S. PATENT DOCUMENTS

| | | |
|---|---|---|
| 5,830,235 A | 11/1998 | Standley |
| 6,033,367 A | 3/2000 | Goldfield |

(Continued)

FOREIGN PATENT DOCUMENTS

| | | |
|---|---|---|
| EP | 2282670 B1 | 4/2013 |
| EP | 3349716 B1 | 2/2019 |

(Continued)

OTHER PUBLICATIONS

Wang et al., Development of a wireless oral-feeding monitoring system for preterm infants, IEEE Journal of Biomedical and Health Informatics, 2015, 19:3, 8 pages.

(Continued)

*Primary Examiner* — Peter R Egloff
(74) *Attorney, Agent, or Firm* — Nixon Peabody LLP

(57) ABSTRACT

Disclosed herein are systems and methods for providing feeding reinforcement in real-time or near real-time based on physiological sensor data acquired during feeding. In some examples, music reinforcement is rendered when one or more feeding features indicative of one or more feeding behaviors are detected using the physiological sensor data. When at least one feature is not detected, the music reinforcement is stopped. In this way, contingent reinforcement is provided in real-time or near real-time based on detection of the one or more feeding behaviors to encourage and improve independent feeding behavior.

22 Claims, 8 Drawing Sheets

(51) Int. Cl.
    *H04R 1/02*     (2006.01)
    *H04R 3/00*     (2006.01)

(56) References Cited

U.S. PATENT DOCUMENTS

| | | | |
|---|---|---|---|
| 6,104,292 A * | 8/2000 | Rombom | A61J 9/00 |
| | | | 340/687 |
| 7,850,504 B2 | 12/2010 | Goldberg et al. | |
| 7,857,677 B2 | 12/2010 | Kamm | |
| 8,287,470 B2 | 10/2012 | Kandori et al. | |
| 8,413,502 B2 | 4/2013 | Zemel et al. | |
| 8,473,219 B2 | 6/2013 | Kaplan et al. | |
| 8,482,416 B2 | 7/2013 | Krans et al. | |
| 9,033,167 B1 | 5/2015 | Pineda et al. | |
| 9,561,002 B2 | 2/2017 | Lau | |
| 9,687,191 B2 | 6/2017 | Chau et al. | |
| 10,004,665 B2 | 6/2018 | Maldonado | |
| 10,186,169 B2 | 1/2019 | Lau | |
| 10,299,718 B2 | 5/2019 | Lau | |
| 10,391,461 B2 | 8/2019 | Alfoudari | |
| 10,434,035 B2 | 10/2019 | Pineda et al. | |
| 10,463,577 B2 | 11/2019 | Lau | |
| 10,555,875 B2 | 2/2020 | Pineda et al. | |
| 10,561,582 B2 | 2/2020 | Wood | |
| 10,682,285 B2 | 6/2020 | Levin | |
| 10,842,718 B2 | 11/2020 | Kessels et al. | |
| 10,888,184 B2 | 1/2021 | Levin | |
| 10,928,228 B2 | 2/2021 | Travers et al. | |
| 11,033,221 B2 | 6/2021 | Chau et al. | |
| 11,077,027 B2 | 8/2021 | Pineda et al. | |
| 11,298,297 B2 | 4/2022 | Wood | |
| 11,324,666 B2 | 5/2022 | Van Kollenburg et al. | |
| 2006/0061985 A1* | 3/2006 | Elkins | A47G 19/2227 |
| | | | 362/253 |
| 2008/0039778 A1 | 2/2008 | Goldie et al. | |
| 2008/0119108 A1 | 5/2008 | Kamm | |
| 2008/0203049 A1 | 8/2008 | Goldberg et al. | |
| 2010/0145166 A1 | 6/2010 | Pickler et al. | |
| 2015/0335533 A1* | 11/2015 | Pineda | A61J 11/002 |
| | | | 215/11.1 |
| 2018/0140510 A1 | 5/2018 | Maldonado | |
| 2018/0197629 A1 | 7/2018 | Zhou | |
| 2019/0096224 A1 | 3/2019 | Shoham et al. | |
| 2020/0121241 A1 | 4/2020 | Hafezi et al. | |
| 2020/0196782 A1 | 6/2020 | Lee et al. | |
| 2021/0052091 A1 | 2/2021 | Lee et al. | |
| 2021/0169398 A1 | 6/2021 | Sorgini et al. | |
| 2021/0369184 A1 | 12/2021 | Tiemann et al. | |
| 2021/0386370 A1 | 12/2021 | Van Der Zwan et al. | |
| 2022/0167930 A1 | 6/2022 | Hannula et al. | |

FOREIGN PATENT DOCUMENTS

| | | |
|---|---|---|
| EP | 3448349 B1 | 10/2019 |
| EP | 3636151 A1 | 4/2020 |
| EP | 3666174 A1 | 6/2020 |
| EP | 3741349 A1 | 11/2020 |
| EP | 3821873 A1 | 5/2021 |
| EP | 3827748 A1 | 6/2021 |
| EP | 2665408 B1 | 8/2021 |
| EP | 3448349 B2 | 8/2022 |
| WO | 2015040610 A2 | 3/2015 |
| WO | 2017056083 A1 | 4/2017 |
| WO | 2018053045 A2 | 3/2018 |
| WO | 2019005740 A1 | 1/2019 |
| WO | 2019036408 A1 | 2/2019 |
| WO | 2020025337 A1 | 2/2020 |
| WO | 2020074716 A1 | 4/2020 |
| WO | 2020120120 A1 | 6/2020 |
| WO | 2020193842 A1 | 10/2020 |
| WO | 2021174020 A1 | 9/2021 |

OTHER PUBLICATIONS

McGrattan et al., Capturing infant swallow impairment on videofluoroscopy: timing matters, Pediatric Radiology, 2019, https?//doi.org/10.1007/s00247-019-04527-w, 8 pages.

ISR and WO for PCT/US2021/019935 dated May 18, 2021, 13 pages.

Poorjavad et al., Surface Electromyographic Assessment of Swallowing Function, Iran Journal of Medical Science, Mar. 2017, 42(2):194-200.

* cited by examiner

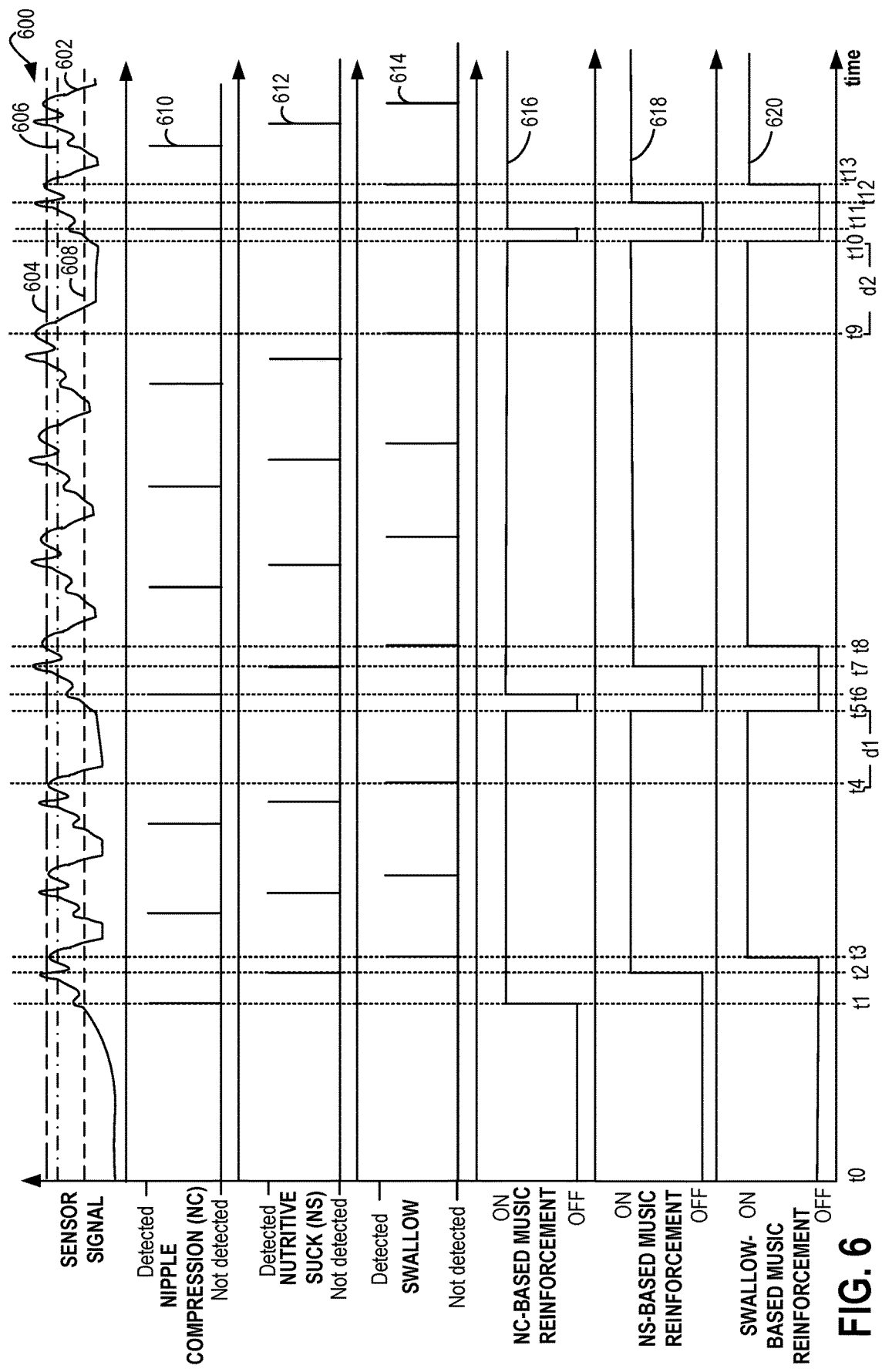

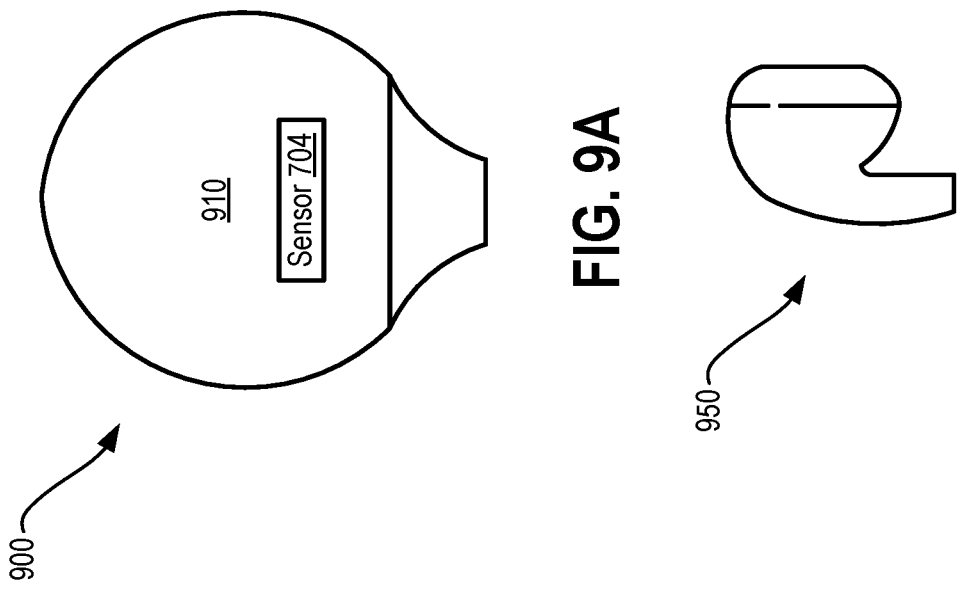
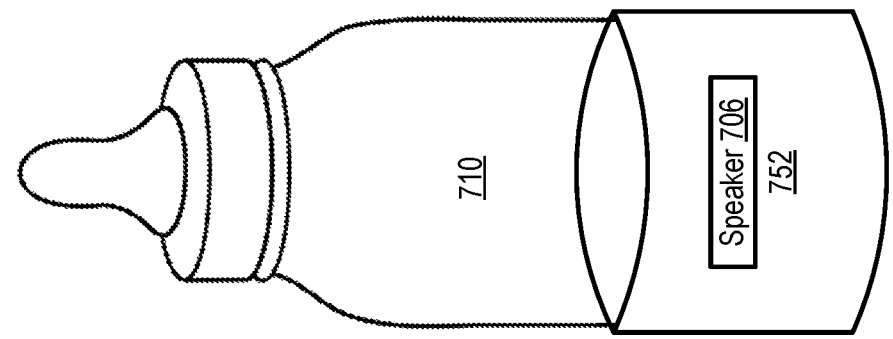
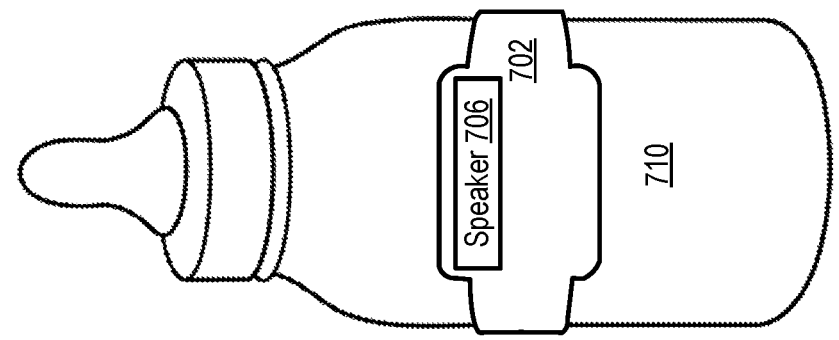

INFANT FEEDING REINFORCEMENT SYSTEM

CROSS-REFERENCE TO RELATED APPLICATIONS

This application is a national phase of International Application No. PCT/US2021/019935, filed Feb. 26, 2021, which designated the U.S. and that International Application was published under PCT Article 21(2) in English. This application claims priority to U.S. Provisional Application No. 62/982,067 filed Feb. 27, 2020, titled "INFANT FEEDING REINFORCEMENT SYSTEM", the contents of which are incorporated herein by reference.

FIELD

The present invention is directed to infant nutrition and behavior systems, and more particularly, to systems and methods for infant feeding reinforcement.

BACKGROUND

The following description includes information that may be useful in understanding the present invention. It is not an admission that any of the information provided herein is prior art or relevant to the presently claimed invention, or that any publication specifically or implicitly referenced is prior art.

Feeding is an important neurodevelopmental milestone and one of the most complex activities in the first months of life. Yet, many infants struggle to develop healthy nutritive sucking and swallowing skills. Research into feeding disorders indicates that up to 45% of normally developing children and up to 80% of developmentally delayed children experience feeding problems. Further, premature infants are almost four times more likely to suffer from feeding problems than full term infants. While premature infants usually demonstrate a suck/swallow/breathe reflex by 34 weeks of post-menstrual age, and the ability to attempt oral feeding by around 35 weeks, many premature infants are unable to take in 100% of feedings orally, which leads to prolonged stays in the neonatal intensive care unit (NICU). This in turn can result in reduced parent-infant bonding opportunities, inhibited neurologic development, and high healthcare costs. Other health and development related issues, such as chronic lung disease, neurologic disorders, increased infections and language delay, are also associated with feeding disorders during infancy.

SUMMARY

Current approaches to address feeding problems in NICU patients and/or in older infants are primarily human-based feeding techniques guided by a clinician (e.g., a feeding specialist, a speech-language pathologist, an occupational therapist, a NICU nurse, a physician, etc.). Most feeding-related issues are treated via a trial and error approach, without any gold-standard or protocol driven care to address such issues. Further, some NICU graduates are unable to sustain normal feeding behavior at home without continuous guidance, thereby forcing expensive hospital readmissions or the need for outpatient feeding therapy. Even some full term infants require frequent feeding therapy visits and due to the trial and error approach, extended time is often needed to establish an acceptable feeding behavior. As a result, the infants may experience weight-loss and other feeding related issues.

Even after establishing an acceptable feeding behavior, when there is a change in the infant's environment or routine, the previously established feeding behavior may be affected. For example, when an infant experiences a change from an at-home environment to a day care environment, the infant may encounter difficulties in adjusting from feeding by a parent to feeding by a caregiver in the day care. Further, in some instances, the type of feeding may be different in different environments. For example, the infant may be breast-fed at home, but in a different environment (e.g., day care), the infant may have to feed from a bottle. Due to the change, the necessary milk intake is reduced, because of the infant's lack of desire and/or skill to bottle feed, which may result in weight loss and increased susceptibility to infections. Furthermore, some full term infants struggle to take nourishment by bottle after having been solely breastfed for many weeks or months after birth. Encouraging the infant to feed from the bottle is often challenging, particularly for the older infants as they develop more awareness with age.

The inventors herein have identified the above-mentioned issues, and provide a system for feeding reinforcement to at least partially address some of the issues. Accordingly, in one example, a system for feeding reinforcement comprises: at least one sensor configured to output physiological data; a sound rendering device; a memory; a control system coupled to the memory, and comprising one or more processors, the control system configured to execute a machine executable code to cause the control system to receive the physiological data output from the at least one sensor; process, in real-time or near real-time, the physiological data to detect one or more feeding features; and render, in real-time or near real-time, an audio content via the sound rendering device responsive to detecting the one or more feeding features; wherein the one or more feeding features includes a nutritive suck event, a swallow event, and/or a nipple compression event. The audio content may be music rendered via the speaker. In this way, reinforcement is provided via the audio content when a desired feeding behavior is detected.

As one example, during feeding, when an infant is feeding from a feeding bottle, physiological data from a sensor may be acquired. The sensor may be coupled to the feeding bottle, or to a wearable component (e.g., bib, skin patch, etc.) that may be placed on the infant, or to a headphone system that may be positioned over or in the infant's ear (e.g., as in the case of an ear-bud). The acquired physiological data is transmitted to a computing system (e.g., a mobile phone), and processed in real-time to output one or more feeding features that indicate a current feeding behavior or pattern. Accordingly, the one or more features may include a nutritive suck event indicating a nutritive suck behavior, which includes drawing liquid nourishment (that is, mother's milk or formula-based milk) from the bottle; a swallow event indicating a swallowing behavior, which includes transport of a liquid bolus through the mouth to the pharynx; and/or a nipple compression event indicating an expression behavior, which includes compression of a nipple of the bottle (between the infant's tongue and a hard palate) to eject the liquid into the mouth. Upon detecting the one or more feeding features from the physiological data, an auditory reinforcement is provided to encourage the infant to continue the feeding behavior. The auditory reinforcement may be provided by rendering an audio content, in real-time via a speaker coupled to the feeding bottle or via a speaker of the computing system. The audio content may include music (e.g., a recording of a lullaby sung by the infant's mother) for reinforcing the detected nutritive sucking, swallowing and/or nipple compression behavior. When none of the feeding features are detected from the physiological data or when a threshold duration has lapsed since a last time point of detection of a feeding feature, the rendering of the audio content is stopped.

In this way, immediate reinforcement is provided to the infant based on real-time physiological data, thereby encouraging the infant to continue feeding from the feeding bottle. Further, the reinforcement is contingent up on detecting a desired feeding behavior or pattern, which further motivates the infant to restart or continue the desired feeding behavior. Thus, through immediate and contingent music reinforcement, infant feeding habits may improve.

Further, the immediate and contingent reinforcement may improve feeding behavior when there is a change in the feeding environment, and enable an infant to adjust more quickly not only to a different feeding environment, but also efficiently switch back and forth between breast-feeding and bottle feeding. Furthermore, the auditory reinforcement that is immediate and contingent eases transition from breast feeding to bottle feeding due to infants' strong preference for music, especially their mother's singing voice, and may encourage healthy bottle feeding behavior.

The above advantages and other advantages, and features of the present description will be readily apparent from the following Detailed Description when taken alone or in connection with the accompanying drawings. It should be understood that the summary above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The accompanying drawings, which are incorporated in and constitute a part of this specification, exemplify the embodiments of the present invention and, together with the description, serve to explain and illustrate principles of the invention. The drawings are intended to illustrate major features of the exemplary embodiments in a diagrammatic manner. The drawings are not intended to depict every feature of actual embodiments nor relative dimensions of the depicted elements, and are not drawn to scale.

FIG. 6 depicts an example sequence illustrating sensing of feeding behavior and reinforcement delivered based on the sensed feeding behavior, according to an embodiment of the disclosure;

FIG. 8A shows an example speaker assembly that is utilized for rendering auditory reinforcement, such as the feeding reinforcement system of FIG. 2, according to an embodiment of the disclosure;

FIG. 8B shows an example speaker assembly that is utilized for rendering auditory reinforcement, such as the feeding reinforcement system of FIG. 2, according to another embodiment of the disclosure;

FIG. 9A shows an example sensor module that is utilized for sensing one or more feeding behaviors, such as the feeding reinforcement system of FIG. 2, according to an embodiment of the disclosure; and FIG. 9B shows an example sensor module that is utilized for sensing one or more feeding behaviors, such as the feeding reinforcement system of FIG. 2, according to another embodiment of the disclosure.

Figure 1:
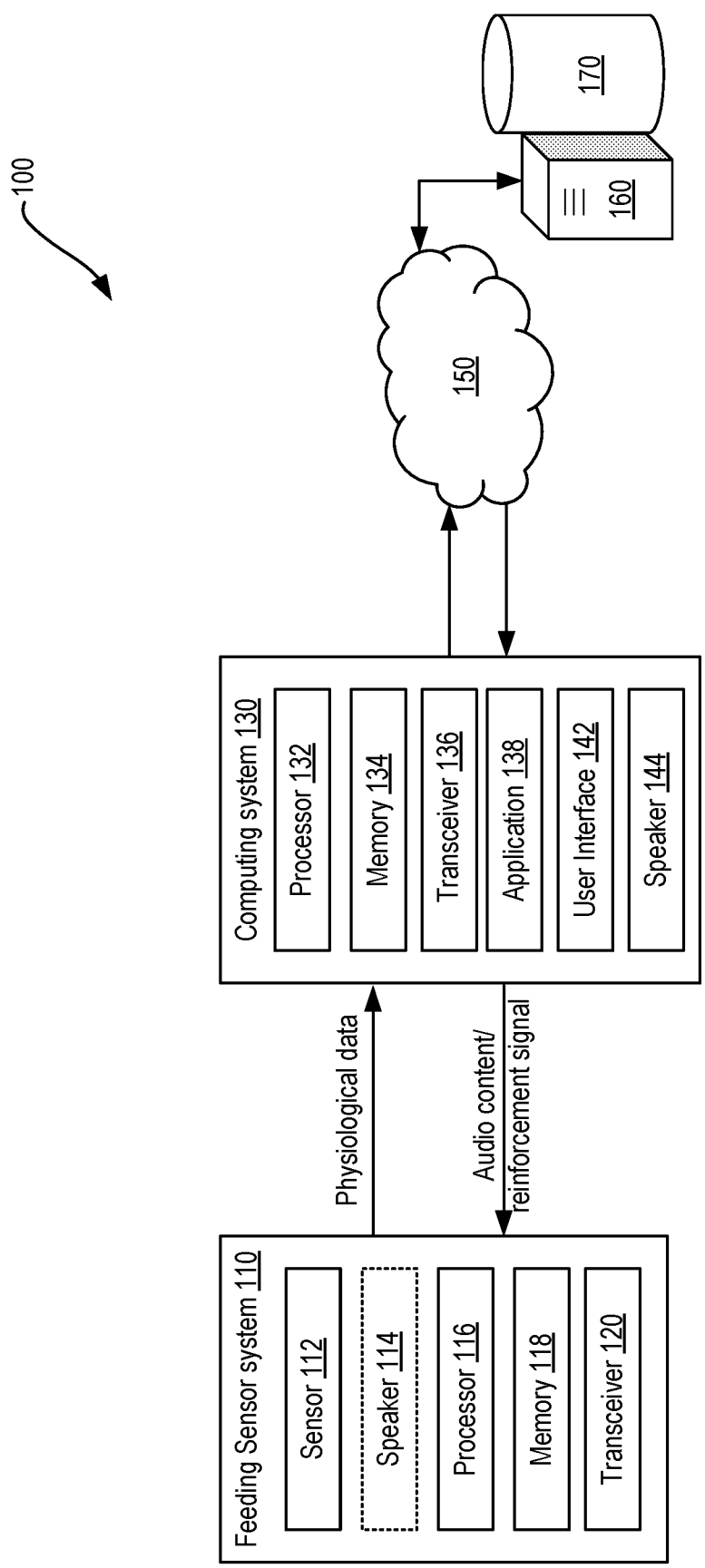
FIG. 1 depicts an example overview of a feeding reinforcement system, according to an embodiment of the disclosure.

In the drawings, the same reference numbers and any acronyms identify elements or acts with the same or similar structure or functionality for ease of understanding and convenience. To easily identify the discussion of any particular element or act, the most significant digit or digits in a reference number refer to the Figure number in which that element is first introduced.

DETAILED DESCRIPTION

Unless defined otherwise, technical and scientific terms used herein have the same meaning as commonly understood by one of ordinary skill in the art to which this invention belongs. One skilled in the art will recognize many methods and materials similar or equivalent to those described herein, which could be used in the practice of the present invention. Indeed, the present invention is in no way limited to the methods and materials specifically described.

In some embodiments, properties such as dimensions, shapes, relative positions, and so forth, used to describe and claim certain embodiments of the invention are to be understood as being modified by the term "about."

As used herein, the term "real-time" is defined to include a process occurring without intentional delay. For purposes of this disclosure, the term "real-time" will additionally be defined to include an action occurring within 2 seconds. For example, if data is acquired, a real-time response (e.g., audio content rendering for reinforcement) based on that data would occur within 2 seconds of the acquisition. Those skilled in the art will appreciate that most real-time processes will be performed in substantially less time than 2 seconds.

As used herein, the term "near real-time" is defined to include a process occurring without intentional delay, given the processing limitations of the system and the time required to acquire the data.

Various examples of the invention will now be described. The following description provides specific details for a thorough understanding and enabling description of these examples. One skilled in the relevant art will understand, however, that the invention may be practiced without many of these details. Likewise, one skilled in the relevant art will also understand that the invention can include many other obvious features not described in detail herein. Additionally, some well-known structures or functions may not be shown or described in detail below, so as to avoid unnecessarily obscuring the relevant description.

The terminology used below is to be interpreted in its broadest reasonable manner, even though it is being used in conjunction with a detailed description of certain specific examples of the invention. Indeed, certain terms may even be emphasized below; however, any terminology intended to be interpreted in any restricted manner will be overtly and specifically defined as such in this Detailed Description section.

While this specification contains many specific implementation details, these should not be construed as limitations on the scope of any inventions or of what may be claimed, but rather as descriptions of features specific to particular implementations of particular inventions. Certain features that are described in this specification in the context of separate implementations can also be implemented in combination in a single implementation. Conversely, various features that are described in the context of a single implementation can also be implemented in multiple implementations separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations may be depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the implementations described above should not be understood as requiring such separation in all implementations, and it should be understood that the described program components and systems can generally be integrated together in a single software product or packaged into multiple software products.

Overview

Figure 2:
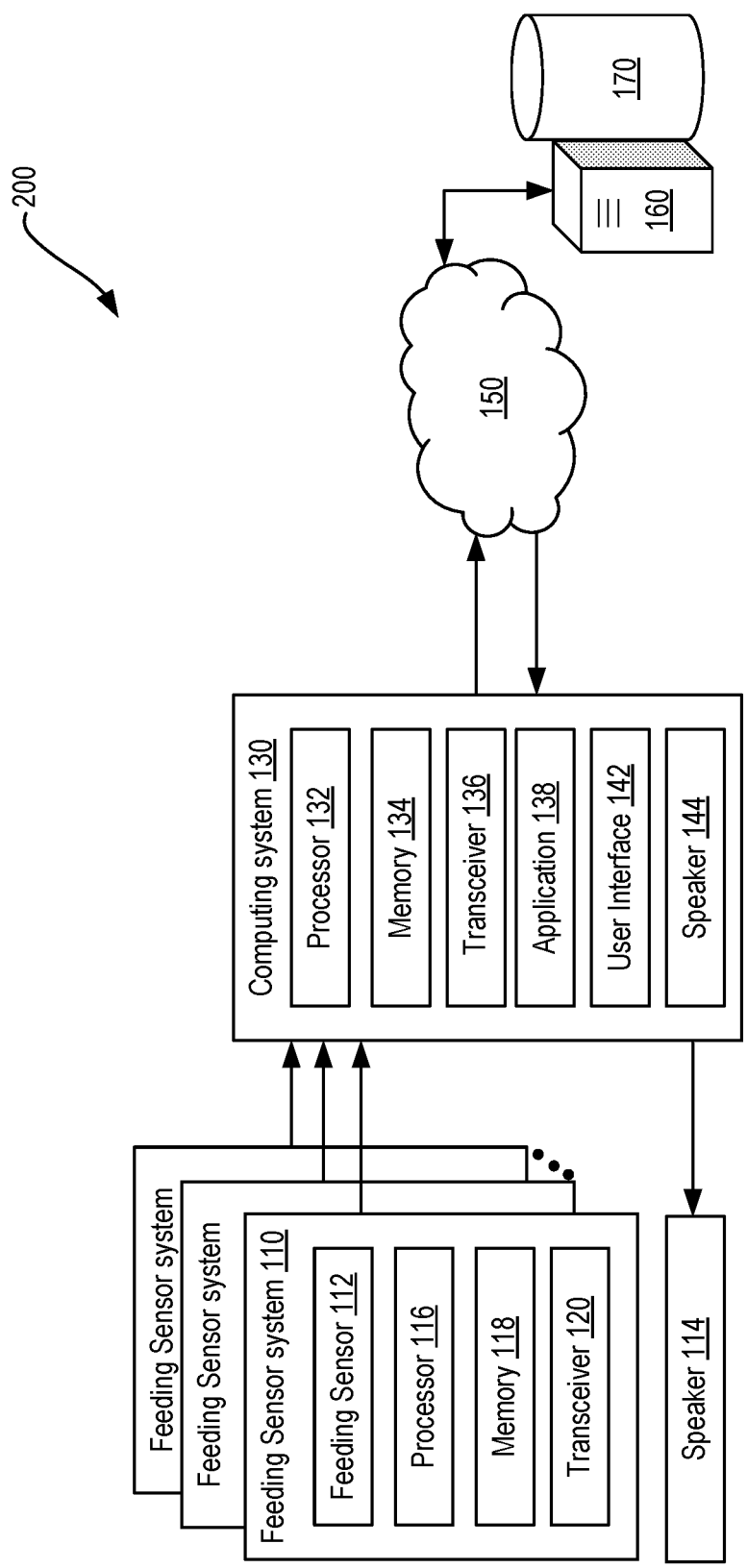
FIG. 2 an example overview of another embodiment of the feeding reinforcement system shown in FIG. 1.
Figure 7B:
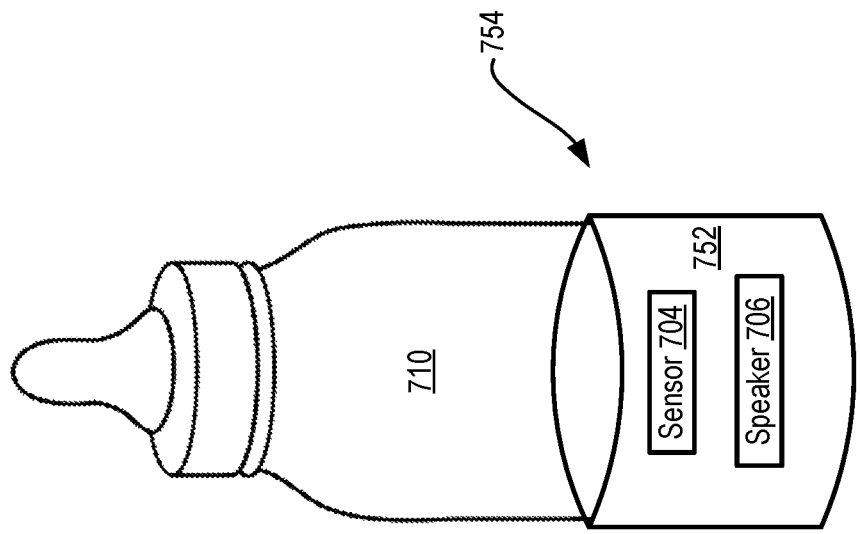
FIG. 7B shows another example feeding sensor system that is utilized in a feeding reinforcement system, such as the feeding reinforcement system of FIG. 1, according to another embodiment of the disclosure.
Figure 7A:
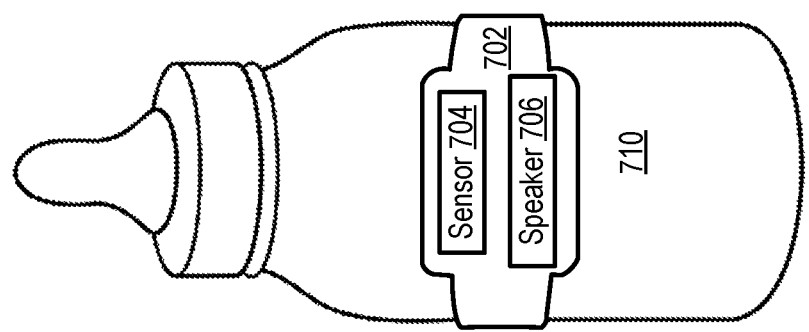
FIG. 7A shows an example feeding sensor system that is utilized in a feeding reinforcement system, such as the feeding reinforcement system of FIG. 1, according to an embodiment of the disclosure.

The present description relates to systems and methods for feeding reinforcement. In particular, the present description relates to systems and methods for providing real-time or near real-time feeding reinforcement during feeding via a feeding bottle. Example overviews of feeding reinforcement systems that may be used for real-time or near real-time feeding reinforcement are shown in FIGS. 1 and 2. The feeding reinforcement system includes a feeding sensor system for acquiring sensor data indicative of one or more feeding behaviors during feeding. Example feeding sensor systems that may be used with a feeding bottle are shown in FIGS. 7A and 7B. In some examples, the feeding sensor system may be configured as a wearable, such as the feeding sensor shown in FIG. 9A, or disposed within a headset as shown in FIG. 9B. A computing system may receive sensor data, process sensor data, and provide feeding reinforcement in real-time or near real-time according to example methods described at FIGS. 3, 4, and 5. Processing the sensor data may include detecting one or more feeding features indicative of the one or more feeding behaviors (e.g., nipple compression, nutritive sucking, and swallowing). The feeding reinforcement may include an auditory reinforcement, which may be provided by rendering an audio content, such as music, during feeding in order to reinforce the detected feeding behavior. Example positioning of a speaker module for delivering reinforcement is shown in FIGS. 8A and 8B. A prophetic feeding sequence that includes providing real-time or near real-time reinforcement according to one or more detected feeding behaviors is shown at FIG. 6. Further, the reinforcement is contingent upon detecting the one or more feeding behaviors, and as such, the reinforcement is provided only when acceptable feeding behavior is detected.

By providing real-time and contingent feeding reinforcement during feeding, an infant may be encouraged to learn to continue the feeding process. The real-time reinforcement also allows the infant to decipher that a certain feeding behavior is beneficial, which enables the infant to continue the feeding. Further, through contingent reinforcement (that is, stopping delivery of audio content when a desired feeding behavior is not detected), when the infant deviates from feeding, the infant is motivated to re-initiate feeding to seek the audio content as a reward. Further, the real-time reinforcement through selected audio content (e.g., mother's singing voice) allows the infant to gain a sense of familiarity and comfort and continue feeding even when there is a change in the environment (e.g., change in the caregiver feeding the infant) and/or change in routine and by providing music at an appropriate tempo (e.g., that of the mature infant suck pattern) it encourages the infant to suck at that mature, healthy rate. In this way, the feeding reinforcement systems and methods described herein greatly advances improvement in the field of pre-term as well as full term infant feeding.

Systems

Referring to FIG. 1, a feeding reinforcement system 100 is shown, in accordance with an exemplary embodiment. The feeding reinforcement system 100 includes a feeding sensor system 110 and a computing system 130. In some embodiments, the computing system 130 may be communicatively coupled to one or more computing devices 170 (e.g., servers, edge devices, etc.) and/or one or more databases 160 via a communication network 150. The network 150 may be wired, wireless, or various combinations of wired and wireless. The one or more computing devices 170 and databases 160 may be local, remote, and any combination thereof.

The feeding sensor system 110 includes at least one sensor 112 for acquiring physiological data. The physiological data acquired via the sensor 112 is used to detect one or more feeding events. The one or more feeding events may include a nutritive suck event, a swallow event, and/or a nipple compression event. In some examples, the physiological data may also be used for detecting one or more feeding patterns based on the one or more feeding events, as further discussed below.

In some embodiments, the sensor 112 may be an audio sensor. When configured as an audio sensor, the sensor 112 may acquire audio data during feeding, and the sounds detected using the audio data correspond to physiological indicators of one or more feeding events. For example, the audio sensor may be used to capture sounds associated with the one or more feeding event. Example sounds associated with feeding include nutritive sucking sounds, swallowing sounds, expiratory burst sounds, glottal release sounds, nipple compression sounds, etc. Depending on the location of the audio sensor, different sounds may be used to detect the one or more feeding events and accordingly, evaluate feeding behavior. In one example, when the audio sensor is disposed in a headphone (e.g., in-ear headphone or over-the ear headphone), example sounds that may be acquired and used for detecting feeding include opening/closing of the Eustachian tube, laryngeal movement, etc.

In some embodiments, the sensor 112 may be an electromyography (EMG) sensor. When configured as an EMG sensor, the sensor 112 may acquire electrical data. In some embodiments, the sensor 112 may be a combination sensor including at least one audio sensor and at least one EMG sensor. In some examples, the sensor 112 may be configured as a pressure sensor, and changes in pressure during feeding detected via the pressure sensor may be used to detect one or more feeding events.

The feeding sensor system 110 may further include a wireless transceiver 120 for transmitting physiological data acquired via the sensor 112 to the computing system 130 and/or receiving signals from the computing system 130. The communication between the feeding sensor system 110 and the computing system 130 may occur in real-time or near real-time. In one example, the feeding sensor system 110 and the computing system 130 may communicate via a Bluetooth Low Energy (BLE) communication protocol. However, it will be appreciated that the communication between the feeding sensor system 110 and the computing system 130 may occur on any wireless network (e.g., via Bluetooth, WiFi, Zigbee, NFC, or other types of wireless technology). In some examples, the feeding sensor system 110 and the computing system may communicate through a wired network or a combination of wired and wireless networks. The signals received from the computing system 130 may include an indication of one or more parameters (e.g., time, duration, etc.) for providing feeding reinforcement and/or one or more parameters for adjustment of audio content (e.g. tempo, volume, pitch, meter, etc.) for the feeding reinforcement. In some examples, the computing system 130 may also transmit activation signals to the feeding sensor to power on, power off, start data acquisition, stop data acquisition, etc.

The feeding sensor system 110 may further include a speaker 114 for providing feeding reinforcement, such as rendering audio content, during feeding based on the signals received from the computing system 130. Additionally, the feeding sensor system 110 may include a power source (not shown), such as a battery, for powering the various operations of the feeding sensor system 110.

The feeding sensor system 110 may further include a processor 116 and non-transitory memory 118 storing machine readable instructions executable by the processor 116. In one example, the processor 116 may receive a signal indicating detection of a feeding event from the computing system 130, responsive to which the processor may cause the speaker 114 to render an audio content as feeding reinforcement. In some examples, the processor 116 may adjust one or more parameters (e.g., tempo, volume, pitch, meter, etc.) of the audio content in order to provide optimal reinforcement. In particular, the one or more parameters of the audio content may be adjusted according to an indication of one or more attributes (e.g., frequency, amplitude, duration, etc.) of a feeding pattern and/or indications of one or more feeding events received from the computing system 130. In some embodiments, the computing system 130 may transmit the audio content and/or adjusted audio content to the feeding sensor system 110. The transmitted audio content and/or the adjusted audio content is then rendered via the speaker 114. In some other embodiments, the speaker 114 may be a smart speaker, and may provide reinforcement and/or adjust the one or more parameters of the audio content rendered during reinforcement based on one or more signals from the computing system 130 and/or the processor 116 of the feeding sensor system.

In one embodiment, the processor 116 may receive the sensor data from the sensor 112, detect a feeding event, and render the audio content in response to detecting the feeding event. Said another way, a computing system including at least one processor and at least one memory may be integrated within the feeding sensor system 110. The computing system integrated with the feeding sensor system 110 is also referred to as "integrated computing system". Accordingly, in one example, the at least one memory may store audio content that may be utilized for rendering during feeding. The computing system integrated with the feeding sensor system 110 may receive, in real-time or near real-time, sensor data from the feeding sensor 112, process, in real-time or near real-time, the sensor data to detect one or more feeding events (e.g., nipple compression, nutritive suck, swallow, feeding pattern based on nipple compression, nutritive suck, swallow or a combination thereof) and responsive to detecting one or more feeding events, render, in real-time or near real-time, audio content via the speaker 114 to provide feeding reinforcement. Communication between the sensor, the integrated computing system, and the speaker may occur via a wired communication protocol (e.g., communications area network (CAN) protocol, Peripheral Component Interconnect Express (PCIE), etc.) or a wireless communication protocol (e.g., wireless network on chip, BLE, Bluetooth, WiFi, Zigbee, etc.), or a combination thereof.

As a non-limiting example, during a set-up condition, the computing device 130 may be used for initial set-up. For example, an application 138, discussed further below, may be utilized by a user (e.g., parent) for recording audio content (e.g., record parent singing voice, or any preferred singing voice). Further, via the application 138, one or more rendering preferences (e.g., render recorded audio content with instrumentation, metronome etc., in the background during rendering for feeding reinforcement, render recorded content only, rendering order, etc.) may be set up for a given feeding sensor system 110. Upon completing the set-up, the audio content recorded during set-up and the preferences for the audio content rendering may be transmitted to the integrated computing system in the feeding sensor system 110. It will be appreciated the audio content may include one or more recorded songs and each recorded song may include its own preference for rendering. Thus, each recorded song along with its rendering may be transmitted to the integrated computing system in the feeding sensor system 110.

After the set-up is complete (that is, after the recorded audio content is transmitted to the integrated computing system in the feeding sensor system 110), the feeding sensor system (that is, the feeding sensor, the speaker, and its integrated computing system) may be used by the user or any caregiver (e.g., baby sitter, daycare provider, grandparent, another parent, etc.,) during feeding for reinforcement without relying on the application 138 or requiring the computing system 130 nearby. Thus, after set-up is complete, the feeding sensor system 110 may function as a stand-alone unit. In one example, when the feeding sensor 112 and the speaker 114 are not disposed within one housing unit, the computing system may be integrated with the sensor or the speaker. In any configuration, one or more power sources (not shown) may be included to supply electrical power to the various components (e.g., individual components or any combination of the feeding sensor, speaker, and computing system) of the feeding sensor system.

By integrating the computing system with the feeding sensor system, usability and user experience is greatly improved. In particular, the feeding sensor system can be used independently, that is, without another piece of equipment (e.g., the computing system 130), allowing for the feeder/caregiver of the infant to be responsible for one less variable in order to feed the infant with the feeding reinforcement device. Further, for infants, reducing the time taken to prepare the feeding system (e.g., time taken to warm the feeding bottle, attach the feeding sensor system, etc.) improves feeding experience. For example, as soon as the infant is ready for feeding, reducing the time taken to prepare the feeding bottle improves not only the feeding experience, but also an amount of nutritive intake by the infant. By utilizing an integrated system, where the feeding sensor system is utilized independent of the computing system utilized for set up, as discussed in the example above, a time taken to initiate feeding by the caregiver with the feeding sensor system is greatly reduced. As a result, infant feeding behavior is further enhanced.

In some embodiments, as shown in FIG. 1, the speaker 114 may be disposed within a sensor unit housing the feeding sensor system 110. Example feeding sensor units including both the sensor 112 and the speaker 114 within sensor unit are shown and described with respect to FIGS. 7A and 7B. In some other embodiments, as shown in FIG. 2, the speaker 114 may not be included within the feeding sensor system and may be disposed in a unit separate from a sensor unit housing the feeding sensor system 110. Examples of individually housed sensor and speaker units are shown and described with respect to FIGS. 8A, 8B, 9A, and 9B.

Turning to FIGS. 7A and 7B, the figures show example configurations of a feeding sensor system, such as the feeding sensor system 110 at FIG. 1, including a feeding sensor module 704 and a speaker assembly 706. FIG. 7A illustrates an example of the feeding sensor system. In this example, the feeding sensor system includes a band unit 702 housing the feeding sensor module 704 and the speaker assembly 706. The band unit 702 may be removably coupled to a feeding bottle 710 and may be attached around a portion of a length of the feeding bottle 710, via an attachment portion (e.g., straps). FIG. 7B illustrates another example of the feeding sensor system. Herein, the feeding sensor system includes a cap unit 752 housing the feeding sensor module 704 and the speaker assembly 706. The cap unit 752 is removably coupled to a bottom portion 754 of the feeding bottle 710. In one example, a cap attachment mechanism (e.g., screw-type mechanism, a sliding mechanism, etc.) may be used to couple the cap unit 752 to the bottom portion. The feeding sensor system shown in FIGS. 7A and 7B may further include a transceiver, at least one processor, and at least one memory as discussed at FIG. 1.

In some embodiments, when the feeding sensor system is configured as a unit that is removably coupled to the feeding bottle as shown in FIGS. 7A and 7B, the feeding sensor module 704 may include at least one audio sensor for sensing feeding sounds during feeding with the bottle having the feeding sensor system.

In some embodiments, a combination of the band unit 702 and the cap unit 752 may be utilized. For example, the band unit 702 may include the feeding sensor module 704 while the cap unit may include the speaker assembly 706, or vice-versa.

Next, FIG. 8A shows an embodiment of the band unit 702, wherein the band unit 702 includes the speaker assembly 706 without a feeding sensor module. Similarly, FIG. 8B shows an embodiment of the cap unit 752, wherein the cap unit 752 houses the speaker assembly 706 but not the feeding sensor module. In such embodiments, wherein the speaker assembly is coupled to the feeding bottle (via the band unit 702 or the cap unit 752), the sensor module may be included within a separate sensor unit as shown in FIGS. 9A and 9B.

Referring next to FIGS. 9A and 9B, example separate sensor units that may be utilized in conjunction with the band unit 702 having the speaker assembly 706 and/or the cap unit 752 having the speaker assembly 706 are shown. FIG. 9A shows the separate sensor unit configured as a wearable unit 900 including the feeding sensor module 704. The wearable unit 900 is shown in this example as a bib that may be coupled to the infant. It will be appreciated that the wearable unit 900 with the feeding sensor module 704 may be a smart bracelet, a smart ring, a patch, a band or other device that suitably could be retained on the infant and/or give access to the infant skin to various sensors on the wearable 910. Accordingly, the sensor module 704 may include at least one audio sensor or at least one EMG sensor or a combination thereof.

In some examples, the wearable unit including the feeding sensor may be an adhesive and stick onto the infant's skin near the temple, in the ear, below and anterior from the ear, where the neck and chin meet, behind the ear, behind the neck, on the chest, or other suitable locations. Further, as discussed above, when the feeding sensor is an audio sensor, the feeding sensor may detect feeding related sounds that include but are not limited to swallow sounds, fluid movement, jaw movement, epiglottic retroflexion, laryngeal movement, expiration noise, and/or other physiological indicators of one or more feeding events, where the one or more feeding events include a nipple compression event, a nutritive sucking event, and/or swallowing event. In some examples, the audio sensor may include one or more microphones, or one or more piezoelectric sensors, or a combination thereof.

FIG. 9B shows the separate sensor unit configured as an in-ear microphone 950 for sensing the one or more feeding features. The in-ear microphone may be placed in the external auditory meatus (that is, ear canal). In some embodiments, the separate sensor unit may include one or more microphones or one or more piezoelectric sensors or any combination thereof that may be included within one or more ear-cups of an over the ear headset or an on the ear headset.

Returning to FIG. 1, the computing system 130 may be any suitable computing device, including a computer, laptop, mobile phone, etc. Accordingly, the computing system 130 may include at least one processor 132, at least one non-transitory memory 134, a wireless transceiver 136, a user interface 142 including a display portion, and a speaker 144. The computing system 130 may detect one or more feeding events based on physiological sensor data received from the feeding sensor system 110, and control a rendering device, such as speaker 114 or speaker 144, to provide feeding reinforcement during feeding.

In one embodiment, as discussed above, the computing system 130 may be utilized for an initial set-up process, and subsequently after the initial set-up, the feeding sensor system 110 may be utilized for receiving sensor data, detecting one or more feeding events and rendering audio content according to the one or more feeding events. The computing system 130 may be used for subsequent updates to set up, as well as reviewing feeding information that was acquired by the feeding sensor system 110 during a feeding period.

The one or more feeding events may include a nipple compression event, a nutritive sucking event, and/or a swallowing event, and may be detected based on respective indicators of the one or more feeding events in the acquired sensor data. The indicators of the nipple compression event may include signals corresponding to nipple compression or to an attempt/preparation of nipple compression. For example, during nipple compression, an infant's jaw moves to compress the nipple via lips, tongue, or gums. Further, the tongue is raised and lowered to generate compression on the nipple. Accordingly, the nipple compression event may be detected based on attributes (e.g., frequency, amplitude, duration) of the sensor data that correspond to the nipple compression. As a non-limiting example, the nipple compression event may be detected based on one or more of sound variations (e.g., when audio sensor is used) and voltage changes (e.g., when EMG sensor is used) indicative of jaw and/or tongue movements during nipple compression.

Similarly, the indicators of the nutritive suck event may include signals corresponding to nutritive sucking performed by the infant or corresponding to an attempt or preparation of the nutritive sucking event. For example, during nutritive sucking the tongue tip elevates while the base of the tongue lowers to create suction between the tongue and the hard palate, and then liquid is extracted (sucked) from the nipple. Subsequently, the tongue base elevates to move an extracted bolus of liquid towards the pharynx. Thus, the nutritive suck event may be detected based on attributes of the sensor data that correspond to one or more sub-events that occur during the nutritive sucking.

Lastly, the indicators of the swallowing event may include signals corresponding to the swallowing performed by the infant. For example, during swallowing, the liquid bolus is transferred to the pharynx, and a series of physiological events occur to ingest the bolus. These include posterior tongue retraction followed by larynx elevation, slight epiglottis deflection, closure of vocal cords, and opening of cricopharyngeus for bolus propulsion into the esophagus. Subsequently, exhalation occurs and the bolus clears the upper esophagus. One or more physiological indicators of swallow may be used, such as the expiratory burst or glottic noise after the swallow, to detect the swallowing event. Additional details of detecting the one or more feeding events will be described below with respect to FIGS. 3-6.

In some embodiments, the computing system 130 may store a feeding application 138. In one example, when executed, the feeding application 138 may display, via the display portion of the user interface, one or more traces of the physiological data from the sensor 112, including indications of one or more feeding events in real-time or near real-time. As a result, a caregiver feeding the infant can visualize, in real-time or near real-time, the various feeding events. The feeding application 138 may also store respective feeding histories of one or more infants. Further, the feeding application may enable a user to record and/or store various audio content that may be used for feeding reinforcement. In some examples, through the feeding application 138, the user may select a desired audio content for feeding reinforcement.

In one example, the computing system 130 may include an application 138, which represents machine executable instructions in the form of software, firmware, or a combination thereof. The components identified in the application 138 may be part of an operating system of the mobile device or may be an application developed to run using the operating system. In one example, application 138 may be a mobile application. The application 138 may also include web applications, which may mirror the mobile application, e.g., providing the same or similar content as the mobile application. In some examples, the application 138 may be utilized for a set-up process and/or a review after feeding reinforcement. The set-up process may include recording audio content that may be used for rendering during feeding. The audio content may include one or more songs, which may be an original song, or based on an available song that is accessible via the application 138 or a combination thereof. In one example, the application 138 may be configured to provide one or more recording parameters to support a user during recording. The one or more recording parameters may include, but not limited to, a guide voice, a metronome click, haptic vibration, visual feedback such as animated lyrics or flashing, and instrumental accompaniment.

Upon completing the set-up, the user may transmit the recorded audio content comprising one or more songs along with corresponding rendering preferences for each of the one or more songs. The rendering preference may include playback information that may be applied during rendering (for feeding reinforcement based on one or more feeding events) when feeding, such as recorded voice only, recorded voice with a selected background audio (e.g., instrumentation, metronome, etc.).

During feeding and/or after feeding, each feeding session data may be recorded, transmitted, and/or stored in one or more of a cloud system, such as cloud server comprising one or more computing devices 170 and one or more databases 160 and a local memory 118 (e.g., in embodiments where the feeding sensor system 110 is operated without the computing device 130, when connection to cloud server is not available, or based on user set-up) of the feeding sensor system 110. In this way, feeding session data may be available for a user to review after feeding.

Feeding session data may be accessible and viewed via the application 138 at a later time after feeding to track the progress of an infant. The feeding session data may include information regarding one or more feeding events (e.g., pattern of one or more feeding events, duration of each feeding event, length of pause between two feeding events, frequency of one or more feeding events during each feeding session, etc.), music reinforcement data (e.g., frequency of audio content rendering, duration of music played, type of music played, overall percentage of reinforcement provided, etc.) and/or overall feeding session data (e.g., start and stop times, length of the feeding session, etc.). The feeding session data may be automatically determined based on the feeding sensor data and/or audio content rendering during feeding. Additionally, in some examples, a user may input information regarding a feeding session. User input information may include caregiver information (e.g., caregiver name), intake information (volume, type of milk, type of bottle, type of nipple used, etc.).

In some embodiments, the computing system 130 may transmit sensor data acquired via the feeding sensor system 110 to the one or more computing devices 170 and/or the one or more databases 160 via a communication network 150 for further processing and storing. As a non-limiting example, the one or more computing devices 170 may include a feeding behavior analytical engine that detects, in real-time or near real-time, the one or more feeding features indicative of the one or more feeding behaviors according to a trained machine learning algorithm. For example, the machine learning algorithm may be trained using a plurality of audio datasets, a plurality of EMG datasets, or a combination thereof, each including labels for the one or more feeding features. While the above example illustrates a supervised learning approach, other machine learning approaches (e.g., unsupervised) may be adopted for training the machine learning algorithms to identify one or more feeding features. Responsive to detecting the one or more feeding features, the one or more computing devices 170 may transmit an indication to the feeding sensor system 110 (e.g., via computing system 130) to provide reinforcement.

Further, in some examples, upon detecting the one or more feeding features, the sensor data and the results for a given feeding session may be stored in the one or more databases. For example, a user may request storage of feeding data (sensor data, detected feeding features and associated time points, time points and duration of reinforcement, type of audio content played, etc.), and in response, the feeding data for given feeding session may be stored in the one or more databases, which may be accessed by an authenticated user.

Next, FIG. 2 shows a feeding reinforcement system 200 according to another exemplary embodiment of the disclosure. The feeding reinforcement system 200 may include one or more feeding sensor systems 110, and accordingly, physiological sensor data may be acquired from sensor 112 in each of the one or more feeding sensor systems 110. Similar features are similarly numbered, and description of the similarly numbered features will not be repeated for the sake of brevity. The physiological sensor data from each sensor may be processed, via the computing system, to detect one or more feeding events and/or one or more feeding patterns based on the one or more feeding events. Further, feeding reinforcement may be provided by rendering audio content via the speaker 114 responsive to detecting one or more feeding events and/or one or more feeding pattern. In one example, as shown in FIG. 2, the speaker 114 may be disposed in a speaker unit separate from the one or more feeding sensor systems 110. In some examples, the speaker 114 may be disposed in any one of the sensor units of the one or more feeding systems 110.

Taken together, the feeding reinforcement systems discussed herein may be utilized to detect various feeding events to provide feeding reinforcement in order to improve feeding habits of infants. The feeding reinforcement is contingent upon detection of the one or more feeding events and/or feeding patterns, as a result of which the infant is encouraged to continue and/or improve feeding. Further, the feeding reinforcement systems may be utilized to adjust one or more parameters of an audio content providing feeding reinforcement to entrain a detected feeding pattern of an infant to the one or more parameters of the audio content to further strengthen and improve feeding behavior. Details of providing feeding reinforcement according to the sensed physiological data are further described below with respect to FIGS. 3-6.

Feeding Reinforcement

Figure 3:
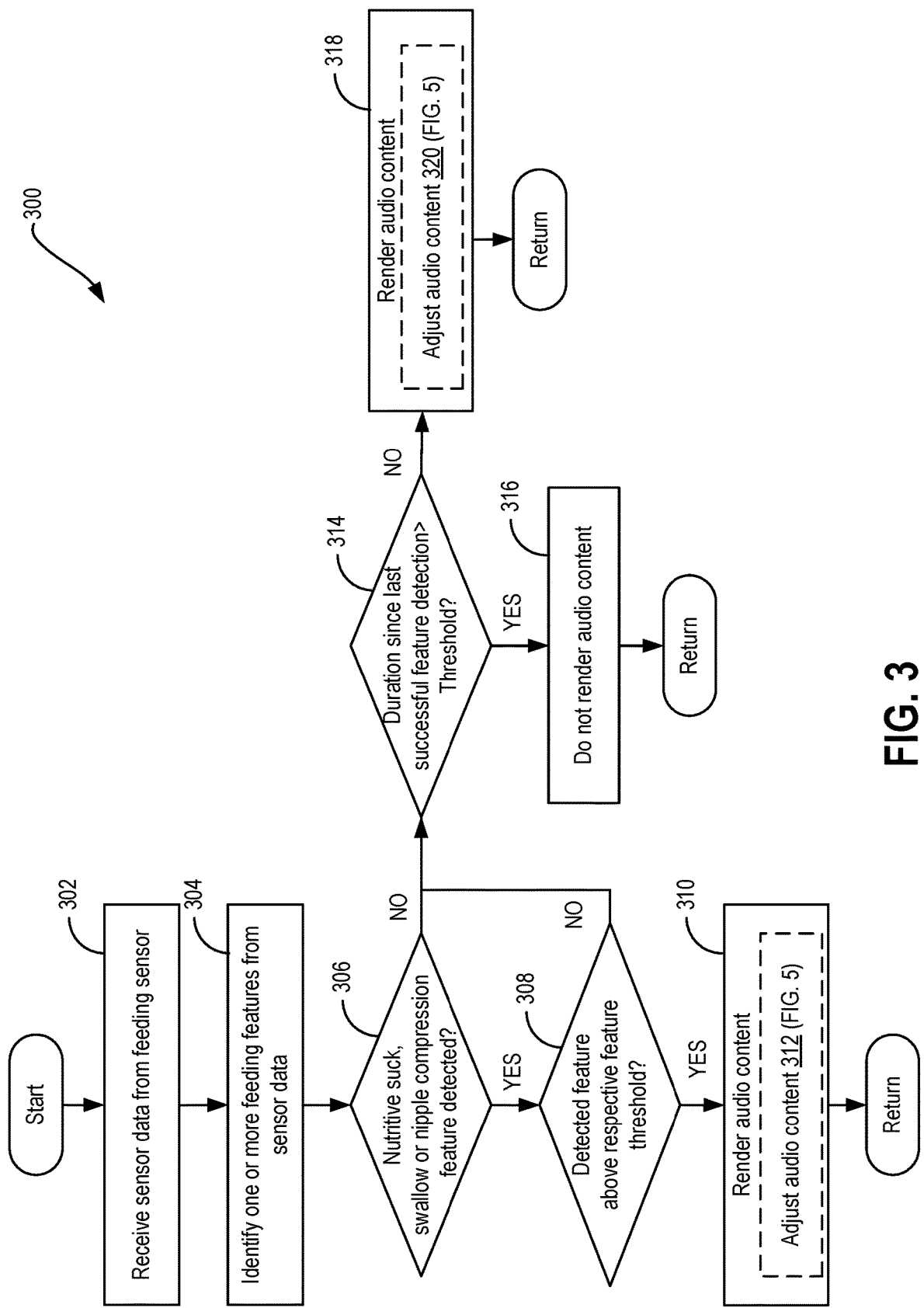
FIG. 3 depicts a flow chart showing an example method for providing feeding reinforcement, according to an embodiment of the disclosure.

FIG. 3 shows a high level flow chart illustrating a method 300 for providing feeding reinforcement by utilizing a feeding reinforcement system, such as the feeding reinforcement system 100 at FIG. 1. While the method 300 and other methods herein are described with respect to FIG. 1, the methods may be implemented by other systems without departing from the scope of the disclosure. The method 300 may be implemented as executable instructions in non-transitory memory, such as memory 134, and may be executed by a processor, such as processor 132, an edge device, a cloud computing system in communication with the processor, or any combination thereof. In some examples, the method 300 may be implemented by a computing system integrated with the feeding sensor system. For example, the method 300 may be implemented as executable instructions in non-transitory memory, such as memory 118, and may be executed by a processor, such as processor 116.

At 302, method 300 includes receiving physiological sensor data from a feeding sensor, such as sensor 112 at FIG. 1. The feeding sensor may be an audio sensor or an EMG sensor, or a combination thereof. Accordingly, the physiological sensor data acquired via the sensor may include audio data or electrical data or a combination thereof.

Next, at 304, method 300 includes processing the physiological sensor data in real-time or near real-time to identify one or more feeding features. Processing the physiological sensor data includes filtering the sensor data to reduce potentially interfering data not indicative of nutritive suck, swallow, and nipple compression events. The potentially interfering data may include data related to head movement, environmental noise, etc. In some examples, data filtering may be performed by the feeding sensor system before transmitting the physiological sensor data.

The filtered data is then processed to identify the one or more feeding features. The one or more feeding features include a nipple compression feature indicative of a nipple compression event, a nutritive suck feature indicative of a nutritive suck event, and a swallow feature indicative of a swallow event. The nipple compression event may include an expression event wherein the nipple is compressed between the tongue and the hard palate to eject milk into the mouth. Accordingly, the nipple compression feature (and therefore, the nipple compression event) may be identified based on a nipple compression signal having one or more of a nipple compression amplitude, frequency and duration within respective nipple compression amplitude, frequency, and duration detection ranges. The nipple compression signals may correspond to indications of one or more of a mouth movement, a jaw movement, and a tongue movement associated with the nipple compression event. The nutritive suck event includes a suction event wherein milk is drawn into the mouth. As such, the nutritive suck feature may be identified based on a nutritive suck signal having one or more of a nutritive suck amplitude, frequency, and duration within respective nutritive suck amplitude, frequency, and duration detection ranges. The nutritive suck signals may correspond to indications of tongue sealing, suction, and/or liquid extraction from the nipple. The swallow event includes transport of the liquid bolus from the mouth to the pharynx, and the swallow feature may be based on a swallow signal having one or more of a swallow amplitude, frequency, and duration within respective swallow amplitude, frequency, and duration detection ranges. The swallow signals may correspond to indications of one or more of an expiratory burst after the swallow and glottic noise during or after the swallow. The detection ranges described above may be utilized to identify presence of the one or more feeding features.

In some embodiments, detection thresholds may be used. Accordingly, each of the one or more feeding features may be detected according to one or more attributes (e.g., amplitude, frequency, and/or duration) greater than respective attribute thresholds.

In some embodiments, the respective attribute thresholds may also be performance thresholds discussed below at step 308.

Upon identifying the one or more feeding features, method 300 proceeds to 306, where it is determined if at least one of the one or more feeding features are detected in the physiological sensor data. If the answer is YES, the method 300 proceeds to 308; otherwise, none of the feeding features are detected and the method 300 proceeds to 314. Step 314 is discussed further below.

At 308, the method 300 includes determining if the one or more detected feeding features are above their respective performance thresholds. For instance, responsive to detecting the nipple compression feature, the nutritive suck feature, and/or swallow feature, the method may determine if the detected nipple compression, the nutritive suck, and/or the swallow features are above a nipple compression performance threshold, a nutritive suck performance threshold, and/or a swallow performance threshold respectively. The evaluation of the detected feeding features with respect to their respective performance thresholds may be utilized to determine whether to render audio content or not. That is, the respective performance thresholds may be used to determine whether the detected feeding feature(s) is at a desirable level for providing reinforcement to encourage the infant to continue the current feeding behavior indicated by the detected feeding feature(s) from the physiological sensor data.

In some embodiments, for each detected feeding feature, one or more attributes may be evaluated to determine if the detected feeding feature is above its performance threshold. The one or more attributes may include a frequency, an amplitude, and a duration of the feeding feature. Accordingly, for a nutritive suck (NS) feature, one or more of the NS amplitude, NS frequency, and NS duration may be compared to one or more of an NS amplitude threshold, an NS frequency threshold, and an NS duration threshold. Similarly, one or more of amplitude, frequency, and duration of a detected swallow feature and/or a nipple compression feature may be compared to respective amplitude, frequency, and duration thresholds.

The performance threshold for each feature may vary, and may be based on one or more of an infant age, a previous and/or current feature pattern (e.g., a previous or current nutritive suck pattern, such as two sucks or one suck per nipple compression-nutritive suck-swallow cycle indicated by a frequency of occurrence of the corresponding nutritive suck feature within respective feeding windows), and a previous and/or current feature strength (e.g., a previous or current suck strength indicated by a previous or current amplitude of the corresponding nutritive suck feature). This follows that the one or more attribute thresholds may also be adjusted according to one or more of the infant age, the feature pattern, and the feature strength. Other factors, such as a known feeding condition, may also be considered when setting the performance thresholds. In some embodiments, the respective performance thresholds may be adjusted in an adaptive manner during a single feeding session. As a non-limiting example, at start, when the infant is beginning to feed, the respective performance threshold may be lower in order to initiate reinforcement to encourage the infant to continue the detected feeding behavior, and after a threshold number of suck-swallow cycles, the respective performance threshold may be increased to adjust the respective performance thresholds based on the current feeding behavior (e.g., current amplitude, current frequency, current duration of the detected feeding features). In some examples, the respective performance thresholds may be increased so as to motivate the infant to improve a current feeding behavior (e.g. to increase a nutritive suck strength, duration, etc.)

In some embodiments, a stringent approach may be implemented for performance evaluation. In this approach, the method 300 may evaluate all the detected feeding features, and confirm that performance thresholds are met (in order to proceed to render audio content) only when all the detected feeding features are above the respective performance thresholds; otherwise, even if one detected feature is not above its respective performance threshold, the method may determine that the detected feeding features are not above the respective thresholds. However, in some embodiments a less stringent approach is implemented, wherein while all the feeding features (that is, nipple compression, nutritive suck, and swallow features) are detected, the method may determine that the performance threshold is met responsive to at least one detected feeding feature increasing above the performance threshold (that is, the performance threshold is met when fewer than all the features are above the respective performance thresholds).

If the answer at 308 is YES, the one or more detected feeding features are above the respective feature performance thresholds, and the method 300 proceeds to 310. At 310, the method 300 includes rendering audio content to reinforce current feeding behavior indicated by the one or more detected feeding features above their respective feeding thresholds. The audio content may include musical content (or music) for encouraging the infant to continue feeding. The music may be a recording of the infant's parent's singing voice, or any recording (e.g. instrumental lullaby, nature sounds, sounds resembling those heard in the womb, vocal music renditions, etc.) suitable for encouraging and/or reinforcing the feeding behavior. Further, as indicated at 312, in some embodiments, one or more parameters of the audio content may be adjusted, which is discussed further below with respect to FIG. 5.

Returning to 308, if the answer at 308 is NO, the one or more detected feeding features are not above the respective performance thresholds, and the method 300 proceeds to 314. In some embodiments, if the answer at 308 is NO, the method 300 may proceed to 316 to stop rendering audio content (if audio content is being rendered) or not initiate delivering audio content (until the one or more detected feeding features increase above their respective performance thresholds). The method 300 may then return to 302 to continue evaluating sensor data in real-time.

Returning to 314, the method 300 includes determining if a duration since last successful feature detection with performance above the respective performance threshold is greater than a threshold duration. In other words, if one or more feeding features having above threshold performance are not detected, it may be determined if the break in feeding is due to an expected or normal feeding break event. For example, infants may take regular breathing breaks during feeding. If the break duration correlates with expected breaks for the infant, then the audio content may continue to be rendered. Accordingly, if the answer at 314 is NO, the method 300 proceeds to 318 to render audio content or continue rendering audio content. Step 318 is similar to step 310.

However, if the duration is greater than the threshold duration (answer at 314 is YES), it may be determined that the feeding has stopped, and in order to encourage the infant to seek reward (that is, the reward of the audio content) through feeding, the method 300 proceeds to 316 at which, the rendering of the audio content is stopped.

In this way, audio content is rendered as a reward when expected and successful feeding behavior is detected (indicated by one or more feeding features above the respective performance thresholds) and is contingent upon detecting the successful feeding behavior. By providing audio content attractive to the infants when the successful feeding behavior is detected, infants are encouraged and motivated to continue the successful feeding behavior. Further, by making the audio content contingent upon the successful feeding behavior and not providing the audio content when the detected feeding behavior is not above the respective performance threshold (or not detected at all), the infants are motivated to seek the reward of audio content through feeding (e.g., continuous feeding, restarting feeding, improving feeding, etc.)

Figure 4:
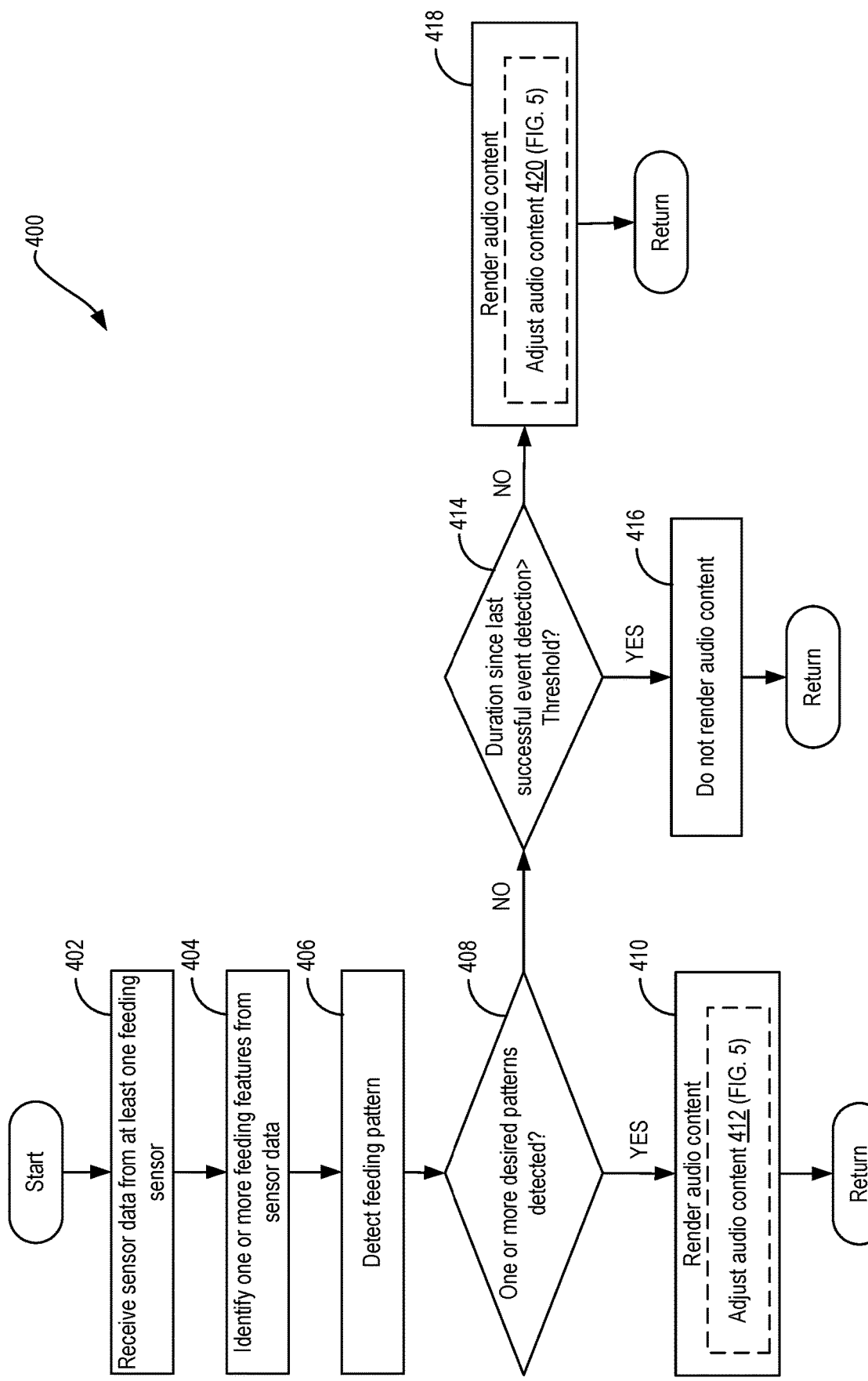
FIG. 4 depicts a flow chart showing an example method for providing feeding reinforcement, according to another embodiment of the disclosure.

Referring to FIG. 4, it shows a high level flow chart illustrating a method 400 for providing feeding reinforcement utilizing a feeding reinforcement system, such as the feeding reinforcement system 100 of FIG. 1. In particular, method 400 may be implemented for providing feeding reinforcement according to a feeding pattern detected using a sensor, such as sensor 112 of the feeding reinforcement system 100. The method 400 may be implemented as executable instructions in non-transitory memory, such as memory 134, and may be executed by a processor, such as processor 132, an edge device, a cloud computing system in communication with the processor, or any combination thereof. In some examples, the method 400 may be implemented by a computing system integrated with the feeding sensor system. For example, the method 400 may be implemented as executable instructions in non-transitory memory, such as memory 118, and may be executed by a processor, such as processor 116. Steps 402, 404, 410, 412, 414, 416, 418, and 420 shown in the method 400 are similar to steps 302, 304, 310, 312, 314, 316, 318, and 320 respectively described at FIG. 3, and therefore, the description of the similar steps will not be repeated.

Briefly, physiological sensor data acquired via the sensor of the feeding reinforcement system is processed in real-time or near real-time to identify one or more feeding features. As discussed above, the one or more feeding features may include a nipple compression feature, a nutritive suck feature, and/or a swallow feature. The one or more feeding features may be detected based on indications of nipple compression, nutritive suck, and/or swallow in the sensor data. In some embodiments, detecting the one or more feeding features may include determining if the one or more feeding features are above their respective performance thresholds and in response, confirming detection of the one or more feeding features.

Upon identifying the one or more feeding features, method 400 proceeds to 406. At 406, the method 400 includes detecting/recognizing one or more feeding patterns based on the one or more detected feeding features. In some embodiments, the one or more feeding patterns may be detected according to respective rates of occurrences of the one or more detected feeding features. As a non-limiting example, a nutritive suck feeding pattern may be detected based on a rate of occurrence of nutritive suck events within a threshold window of duration. Similarly, swallow patterns and/or nipple compression patterns may be detected according to rates of occurrence of swallow events and/or nipple compression events respectively within the threshold window of duration.

In some embodiments, the one or more feeding patterns may be based on a combination of two or more detected feeding features occurring within a number of feeding cycles. As a non-limiting example, the method may include detecting one or more of a nutritive suck-swallow pattern, a nipple compression-swallow pattern, and a nipple compression-nutritive suck-swallow pattern. For instance, an example nutritive suck-swallow pattern may be a suck-suck-swallow pattern. An infant may be unable to draw sufficient milk with one suck and may adopt a suck-suck-swallow pattern of feeding. Accordingly, the method may include recognizing different patterns of feeding.

Next, at 408, the method 400 includes determining if one or more desired patterns are detected. The one or more desired patterns may be based on desired and/or expected feeding behaviors. Accordingly, in some embodiments, the desired pattern may include a desired rate of occurrence of the one or more feeding features, a desired combination of at least two or more feeding features, and/or a desired rate of occurrence of the desired combination.

If one or more desired feeding patterns are detected, the method 400 proceeds to 410 to render audio content in order to encourage the infant to continue feeding. If the one or more desired feeding patterns are not detected, the method may proceed to 414. At 414, as discussed with respect to 314, a break duration based on an expected break duration for an infant is taken in to account in order to determine whether to continue providing the audio content or stop providing the audio content. The expected or reference break duration indicates a time period during which the infant may stop feeding in order to breathe, etc., and may be determined according to one or more of an infant age and a feeding pattern. If the break duration is greater than a threshold duration, the answer at 414 is YES, and the method 400 proceeds to 416. At 416, the method includes stopping the rendering of the audio content. Otherwise, if the answer at 414 is NO, the method proceeds to 418 to render the audio content. Rendering the audio content may further include adjusting one or more parameters of the audio content according to the feeding pattern. Details of adjusting the audio content is discussed below at FIG. 5.

Returning to 408, alternatively, in some embodiments, if the one or more desired feeding patterns are not detected, the method 400 may directly proceed to 416. At 416, as discussed above, the method 400 includes stopping the rendering of the audio content. Thus, the auditory reinforcement, via rendering audio content, is provided in a contingent manner when the one or more desired feeding pattern is detected. Additionally, or alternatively, contingent reinforcement is provided when respective feeding performance of the one or more detected feeding features are above respective performance thresholds (as discussed with respect to FIG. 3). In this way, through contingent reinforcement during feeding based on real-time sensor data indicating the various feeding events, appropriate feeding behavior is reinforced.

Figure 5:
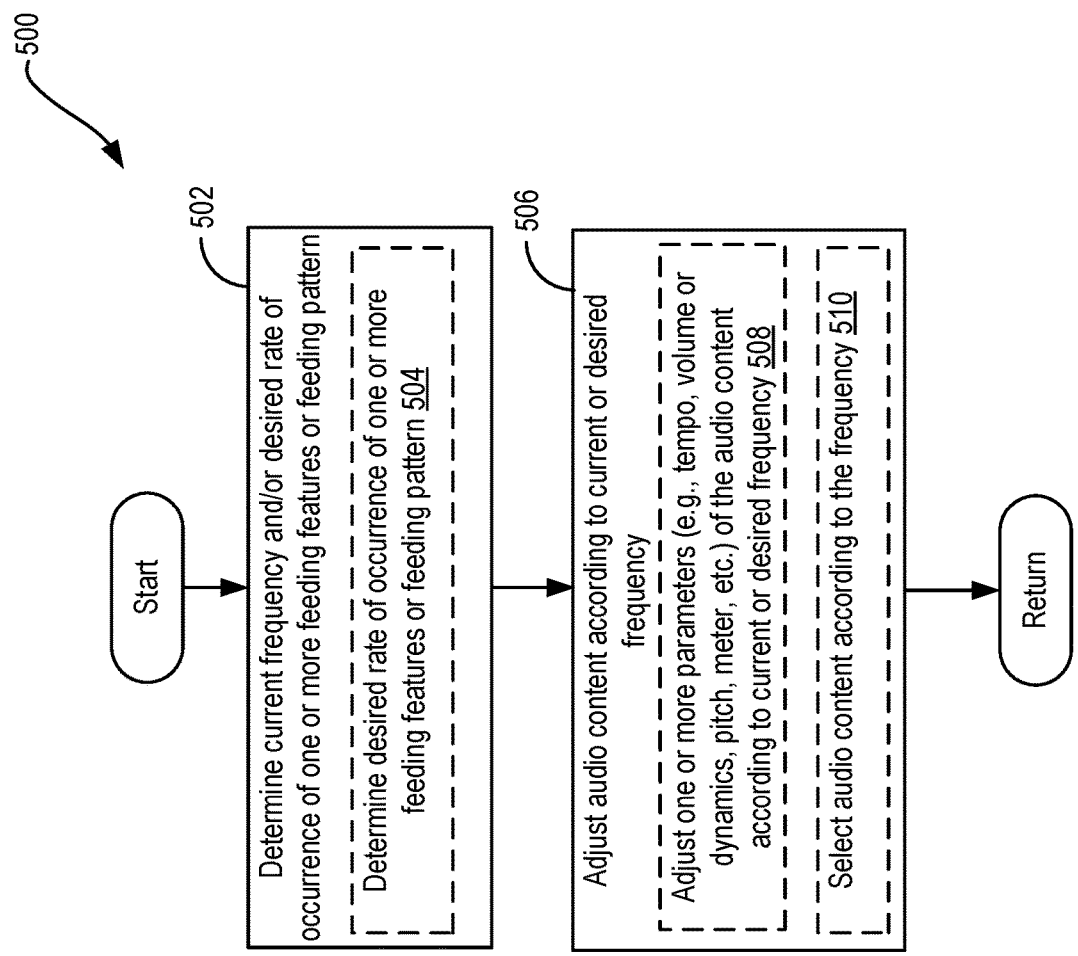
FIG. 5 depicts a flow chart showing an example method for rendering audio content for feeding reinforcement, according to an embodiment of the disclosure.

FIG. 5 shows a high-level flow chart illustrating a method 500 for adjusting one or more parameters of the audio content during feeding based on physiological sensor data, according to an embodiment. Method 500 may be implemented as executable instructions in non-transitory memory, such as memory 134, and may be executed by a processor, such as processor 132, an edge device, a cloud computing system in communication with the processor, or any combination thereof. In some embodiments, the processor may send information regarding desired adjustments to a second processor (e.g., processor 116) of a feeding sensor system communicably coupled to a speaker (e.g., speaker 114) rendering the audio content, and the adjustments may be made by the second processor. In some embodiments, the method 500 may be implemented by a computing system integrated with the feeding sensor system. For example, the method 500 may be implemented as executable instructions in non-transitory memory, such as memory 118, and may be executed by a processor, such as processor 116.

At 502, the method 500 includes determining a current rate (or frequency) of occurrence of the one or more detected feeding features (e.g., the one or more feeding features identified at step 304 of FIG. 3). For instance, a current rate of occurrence of a nutritive suck feature may be determined. Additionally, or alternatively, rates of occurrences of a swallow feature and/or a nipple compression feature may be determined. In some embodiments, a current frequency of a feeding pattern of at least two detected features may be determined (e.g., frequency of a nutritive suck-swallow pattern).

In some embodiments, as indicated at 504, a desired rate of occurrence of the one or more detected feeding features and/or a desired frequency of a feeding pattern of at least two detected feeding features may be determined. The desired rate and/or desired frequency may be determined according to an age of the infant, previous rate of feeding feature and/or frequency of feeding pattern of the infant (e.g., based on a previous higher rate identified for the infant).

Next, at 506, the method 500 includes adjusting one or more parameters of the audio content according to the current rate and/or desired rate of the one or more feeding features and/or pattern. In particular, one or more parameters of the audio content may be adjusted in order to entrain a feeding pattern with the one or more elements of the audio content. The one or more parameters may be one or more elements of music that may be adjusted individually or in combination with one or more other elements of music in order to allow the infant to entrain their feeding pattern with the one or more parameters of the music. The one or more elements of music include rhythm, dynamics, melody, harmony, tone, texture, and form. In one example, one or more aspects of the rhythm may be adjusted, the one or more aspects including a duration (of sound or silence in the audio content), a tempo, and a meter. In another example, additionally or alternatively to adjusting one or more aspects of the rhythm, one or more other elements (e.g., dynamics, melody, harmony, tone, texture, and form) may be adjusted.

As a non-limiting example, a tempo of the audio content may be initially adjusted to 60 beats per minute and the tempo may be increased or decreased according to a current nutritive suck rate determined from the physiological sensor data. In some examples, for younger pre-term infants, the tempo may be reduced. In particular, some younger pre-term infants may have under developed oral feeding ability and may be sucking at a lower rate, and accordingly, the audio content rendered may be adjusted to a lower tempo (e.g., 50 beats per minute). However, in some examples, when the infant suck rate is lower than a threshold, a slow tempo (e.g., 36 beats per minute) may be too slow for the infant to recognize the pulse, and as such, the tempo may be adjusted to a higher rate (e.g., 72 beats per minute). In this example, the infant may suck every two beats of the audio content.

In some embodiments, as indicated at 510, instead of adjusting one or more parameters of the audio content, the audio content may be chosen based on the feeding rate and/or feeding pattern rate. For example, for younger pre-term infants who have a very low suck rate, audio content that has a tempo of 72 beats per minute may be chosen whereas for full term infants, who have a normal suck rate, a different audio content that has a tempo of 60 beats per minute may be chosen.

FIG. 6 shows a prophetic feeding sequence during which conditional reinforcement is provided in real-time or near real-time through conditional rendering of an audio content. In particular, the conditional rendering of the audio content is based on detection of one or more feeding features using physiological sensor data acquired in real-time or near real-time via a physiological sensor, such as sensor 112 at FIG. 1. The one or more feeding features may include one or more of a nipple compression event, a nutritive suck event, and/or a swallow event. In some embodiments, the one or more feeding features may include one or more feeding patterns.

The vertical markers at times t0-t13 represent times of interest during the feeding sequence. In each plot, the horizontal axis represents time and time increases from the left side of the plot to the right side of the plot.

The first plot from the top of FIG. 6 is a plot of audio signal versus time and shows an audio signal trace 602. The audio signal is based on audio data acquired via an audio sensor during feeding. The audio sensor is an example of sensor 112 of the feeding sensor system 110 at FIG. 1. The audio signal is utilized to detect/identify one or more feeding features during feeding. The vertical axis represents an estimate of amplitude of the audio signal and the estimated amplitude increases in the direction of the vertical axis arrow. The present example shows time-domain representation of the sound signal (amplitude versus time). In some embodiments, a transformation may be applied to generate a frequency domain representation of the sound signal, which may be used to identify the one or more feeding features (that is, nipple compression, nutritive suck, and swallow)

Further, while the present example is illustrated using the audio signal based on the audio data from the audio sensor, sensor data from other types of sensors that provide indications of various feeding events during feeding may be used. As a non-limiting example, electrical signal from EMG sensor may be used to detect the one or more feeding features. In some examples, data from more than one sensor may be used. As a non-limiting example, a first sensor may be an audio sensor acquiring audio data, and a second sensor may be an EMG sensor acquiring electrical data. In such examples, both audio data and electrical data may be correlated to determine the one or more feeding features. In still another example, different sensors may be used to detect different feeding features. As a non-limiting example, audio data from an audio sensor may be used to detect a swallow feature while electrical data from an EMG sensor may be used to detect a nutritive sucking behavior.

Horizontal line 604 represents a nutritive suck limit above which a feature is confirmed. Horizontal line 606 represents a swallow limit above which a swallow feature is confirmed. Horizontal line 608 represents a nipple compression limit above which a nutritive suck feature is confirmed. In this example, the limits indicated by 604, 606, and 608 are thresholds for detection as well as performance. It will be appreciated that in some embodiments, the thresholds for detection may be different from performance thresholds. For example, lower thresholds may be used to confirm detection of the one or more feeding features; however, music reinforcement may be provided only when higher thresholds for performance are met.

Further, the audio signal trace and the thresholds 604, 606, and 608 are shown for illustrating when music reinforcement is provided. It will be appreciated that the thresholds may be greater or lower, and the relativity of the thresholds as well as parameters (e.g., amplitude, frequency, duration, etc.) of signal trace may vary depending on the sensor configuration.

The second plot from the top of FIG. 6 is a plot of nipple compression feature (or event) versus time. The vertical axis represents a nipple compression feature (or event) detection state. The nipple compression feature is detected when the nipple compression trace 610 is at a higher level. The nipple compression feature is not detected when the nipple compression trace 610 is at a lower level near the horizontal axis.

The third plot from the top of FIG. 6 is a plot of nutritive suck feature (or event) versus time. The vertical axis represents a nutritive suck feature (or event) detection state. The nutritive suck feature is detected when the nutritive suck trace 612 is at a higher level. The nutritive suck feature is not detected when the nutritive suck trace 612 is at a lower level near the horizontal axis.

The fourth plot from the top of FIG. 7 is a plot of swallow feature (or event) versus time. The vertical axis represents a swallow feature (or event) detection state. The swallow feature is detected when the swallow trace 614 is at a higher level. The swallow feature is not detected when the swallow trace 614 is at a lower level near the horizontal axis.

The fifth, sixth, and seventh plots from the top of FIG. 6 are plots of music reinforcement status versus time. The vertical axis represents a music reinforcement status. Trace 616 shows music reinforcement state according to the nipple compression feature (NC-based music reinforcement); trace 618 shows music reinforcement state according to the nutritive suck feature (NS-based music reinforcement); and trace 620 shows music reinforcement state according to the swallow feature (swallow-based music reinforcement). The music reinforcement is provided when music reinforcement trace (614, 616, or 618) is at a higher level. The music reinforcement is not provided when the music reinforcement trace (614, 616, or 618) is at a lower level near the horizontal axis.

At t0, and between t0 and t1, the sensor signal (trace 602) is below the feature thresholds 604, 606, and 608 and without any indications of any of the feeding features. Thus, none of the feeding features are detected. For example, an infant may start the feeding process at t0 but may not be actively feeding between t0 and t1. As such, the sensor signal may not include indications of the feeding features. When none of the feeding features are detected, the music reinforcement is not provided.

At t1, the infant may initiate a nipple compression, and an indication of the nipple compression is detected using the sensor signal (plot 602) at t1. The indication of nipple compression may be detected based on one or more characteristics of the sensor signal, including amplitude, duration (that is, width), and/or frequency, for example. Further, the indication of the nipple compression at t1 is above the nipple compression threshold 608. Thus, a nipple compression feature is confirmed, and consequently, a nipple compression event is confirmed at t1 (trace 610). In one embodiment, as indicated by trace 616, music reinforcement is provided in response to detecting the nipple compression feature via the sensor signal. In other embodiments, the music reinforcement is provided/initiated when other features, such as nutritive suck or swallow features, or a pattern, such as nipple compression-nutritive suck-swallow, or a combination of at least two features are detected.

At t2, following the nipple compression, the infant may show a nutritive suck behavior, and an indication of the nutritive suck is detected at t2 based on one or more characteristics corresponding to the nutritive suck (e.g., frequency, amplitude, and/or duration) in the sensor signal. Further, the indication of the nutritive suck is above the nutritive suck threshold 604, and in response a nutritive suck feature is confirmed at t2 (trace 612). If music reinforcement is initiated at t1, responsive to detecting the nutritive suck feature, the music reinforcement is continued at t2. In some embodiments, as shown by trace 618, if the music reinforcement is not initiated at t1, the reinforcement may be initiated at t2 responsive to detecting the nutritive suck or responsive to detecting the nutritive suck after the nipple compression at t1.

At t3, following the nutritive suck, the infant may show a swallow behavior indicated at t3 according to one or more characteristics corresponding to the swallow (e.g., frequency, amplitude, and/or duration) in the sensor signal. Further, the indication of the swallow is above the swallow threshold 606, and in response a swallow feature is confirmed at t3 (trace 614). In one embodiment, if music reinforcement is provided/or initiated at t1 or t2, the music reinforcement is continued at t3 responsive to detecting the swallow feature. In some embodiments, the music reinforcement is initiated at t3 responsive to detecting the swallow feature or responsive to detecting nipple compression-nutritive suck-swallow pattern (that is, at time points t1, t2, and t3) or responsive to detecting nutritive suck-swallow (at time points t2 and t3).

Between t3 and t4, one or more of the nipple compression, nutritive suck, and the swallow features and/or one or more feeding patterns are detected, and as such, the music reinforcement is continually provided. In some examples, as discussed with respect to FIG. 5, during feeding while music is provided, one or more elements of the music may be adjusted to enable the infant to recognize and entrain with the music. Further, between each nipple compression-suck-swallow cycle, a nominal break is detected (indicated by lack of feeding features). The nominal break is part of the feeding cycle and corresponds to an expected resting period between each nipple compression-suck-swallow cycle. Thus, during this resting period, even though no feeding features are detected, the music reinforcement is provided.

After the swallow at t4, the infant may stop feeding. At t5, a break duration d1 (when no feeding features and/or patterns are detected) increases above a nominal break duration, and thus, it is confirmed that the feeding has stopped. Responsive to the break duration increasing above the nominal break duration, the music reinforcement is stopped at t5. In this way, a desired feeding behavior is encouraged by providing music reinforcement only when the one or more feeding features and/or one or more feeding patterns are detected; and when any of the feeding features and/or patterns are not detected for a duration greater than the nominal break duration, the music reinforcement is stopped.

At t6, the infant may re-initiate feeding. Responsive to detecting the nipple compression feature at t6, the music reinforcement is re-started at t6 (trace 616). In another embodiment, responsive to detecting the nutritive suck feature at t7 or the nipple compression-suck pattern, the music reinforcement is re-started at t7 (trace 618). In yet another embodiment, responsive to detecting the swallow feature at t8, or any combination of nipple compression, nutritive suck, and/or swallow, the music reinforcement is re-started at t8 (trace 620).

Between t8 and t9, the infant may continue feeding indicated by nipple compression, nutritive suck and swallow features. Further, between t8 and t9, the respective strengths of nipple compression, nutritive suck, and swallow features is greater indicating a stronger feeding behavior. The nominal break duration during the second feeding cycle (after re-initiation) is also slightly longer. In order to allow for the change in feeding behavior, the threshold break duration beyond which the music is stopped is adjusted (that is, increased in this example).

After t9, the infant may again stop feeding, and at t10 the break duration may increase above the nominal adjusted break duration d2. In response to the break duration increasing above d2, the music is stopped at t10. Next, when the feeding re-starts at t11, the music is restarted at t11 for nipple compression based music reinforcement, or at t12 for nutritive suck based music reinforcement, or t13 for swallow based music reinforcement (or any combination of nipple compression, nutritive suck, and/or swallow based music reinforcement).

In this way, music is provided conditionally to the infant responsive to detecting a desired feeding behavior, which may motivate the infant to feed continuously and seek continuous reward (that is, music). As a result, overall feeding behavior is improved.

In one implementation, the feeding system and the methods for feeding reinforcement may be utilized for feeding reinforcement during breast feeding. As a non-limiting examples, a feeding sensor, such as feeding sensor module 900 and 950 at FIGS. 9A and 9B, may be utilized to acquire feeding data during breast feeding. The feeding data may include information regarding one or more feeding events as discussed herein, the one or more feeding events including a nipple compression event, a nutritive suck event, a swallow event, and/or a feeding pattern based on the one or more feeding events. Music reinforcement may be provided via an associated speaker system or a speaker of the computing device (e.g., mobile phone speaker). It will be appreciated that the methods and systems described herein with respect to the feeding bottle, may be applied to music reinforcement during breast feeding, without departing from the scope of the disclosure. In one example, a system for feeding reinforcement may comprise at least one sensor configured to output physiological data; a sound rendering device; a memory; a control system coupled to the memory, and comprising one or more processors, the control system configured to execute a machine executable code to cause the control system to: receive the physiological data output from the at least one sensor; process, in real-time or near real-time, the physiological data to detect one or more feeding features; and render, in real-time or near real-time, an audio content via the sound rendering device responsive to detecting the one or more feeding features; wherein the one or more feeding features includes a nutritive suck event, a swallow event, and/or a nipple compression event. In one non-limiting example, the at least one sensor may be disposed within a wearable component, the wearable component attachable to a subject. The wearable may be a bib, a smart bracelet, a smart ring, a patch, a band or other device that suitably could be retained on an infant and/or on a caregiver (e.g., breast feeding mother).

Computer & Hardware Implementation of Disclosure

It should initially be understood that the disclosure herein may be implemented with any type of hardware and/or software, and may be a pre-programmed general purpose computing device. For example, the system may be implemented using a server, a personal computer, a portable computer, a thin client, a wearable device, a digital stethoscope, or any suitable device or devices. The disclosure and/or components thereof may be a single device at a single location, or multiple devices at a single, or multiple, locations that are connected together using any appropriate communication protocols over any communication medium such as electric cable, fiber optic cable, or in a wireless manner.

It should also be noted that the disclosure is illustrated and discussed herein as having a plurality of modules which perform particular functions. It should be understood that these modules are merely schematically illustrated based on their function for clarity purposes only, and do not necessary represent specific hardware or software. In this regard, these modules may be hardware and/or software implemented to substantially perform the particular functions discussed. Moreover, the modules may be combined together within the disclosure, or divided into additional modules based on the particular function desired. Thus, the disclosure should not be construed to limit the present invention, but merely be understood to illustrate one example implementation thereof.

The computing system can include clients and servers. A client and server are generally remote from each other and typically interact through a communication network. The relationship of client and server arises by virtue of computer programs running on the respective computers and having a client-server relationship to each other. In some implementations, a server transmits data (e.g., an HTML page) to a client device (e.g., for purposes of displaying data to and receiving user input from a user interacting with the client device). Data generated at the client device (e.g., a result of the user interaction) can be received from the client device at the server.

Implementations of the subject matter described in this specification can be implemented in a computing system that includes a back-end component, e.g., as a data server, or that includes a middleware component, e.g., an application server, or that includes a front-end component, e.g., a client computer having a graphical user interface or a Web browser through which a user can interact with an implementation of the subject matter described in this specification, or any combination of one or more such back-end, middleware, or front-end components. The components of the system can be interconnected by any form or medium of digital data communication, e.g., a communication network. Examples of communication networks include a local area network ("LAN") and a wide area network ("WAN"), an inter-network (e.g., the Internet), and peer-to-peer networks (e.g., ad hoc peer-to-peer networks), and any wireless networks.

Implementations of the subject matter and the operations described in this specification can be implemented in digital electronic circuitry, or in computer software, firmware, or hardware, including the structures disclosed in this specification and their structural equivalents, or in combinations of one or more of them. Implementations of the subject matter described in this specification can be implemented as one or more computer programs, i.e., one or more modules of computer program instructions, encoded on computer storage medium for execution by, or to control the operation of, data processing apparatus. Alternatively or in addition, the program instructions can be encoded on an artificially-generated propagated signal, e.g., a machine-generated electrical, optical, or electromagnetic signal that is generated to encode information for transmission to suitable receiver apparatus for execution by a data processing apparatus. A computer storage medium can be, or be included in, a computer-readable storage device, a computer-readable storage substrate, a random or serial access memory array or device, or a combination of one or more of them. Moreover, while a computer storage medium is not a propagated signal, a computer storage medium can be a source or destination of computer program instructions encoded in an artificially-generated propagated signal. The computer storage medium can also be, or be included in, one or more separate physical components or media (e.g., multiple CDs, disks, flash memory, or other storage devices).

The operations described in this specification can be implemented as operations performed by a "data processing apparatus" on data stored on one or more computer-readable storage devices or received from other sources.

The term "data processing apparatus" encompasses all kinds of apparatus, devices, and machines for processing data, including by way of example a programmable processor, a computer, a system on a chip, or multiple ones, multi-core processors, GPUs, AI-accelerators, In-memory computing architectures or combinations, of the foregoing. The apparatus can include special purpose logic circuitry, e.g., an FPGA (field programmable gate array) or an ASIC (application-specific integrated circuit). The apparatus can also include, in addition to hardware, code that creates an execution environment for the computer program in question, e.g., code that constitutes processor firmware, a protocol stack, a database management system, an operating system, a cross-platform runtime environment, a virtual machine, or a combination of one or more of them. The apparatus and execution environment can realize various different computing model infrastructures, such as web services, distributed computing and grid computing infrastructures, and deep learning and artificial intelligence computing infrastructure.

A computer program (also known as a program, software, software application, script, or code) can be written in any form of programming language, including compiled or interpreted languages, declarative or procedural languages, and it can be deployed in any form, including as a stand-alone program or as a module, component, subroutine, object, or other unit suitable for use in a computing environment. A computer program may, but need not, correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub-programs, or portions of code). A computer program can be deployed to be executed on one computer or on multiple computers that are located at one site or distributed across multiple sites and interconnected by a communication network.

The processes and logic flows described in this specification can be performed by one or more programmable processors executing one or more computer programs to perform actions by operating on input data and generating output. The processes and logic flows can also be performed by, and apparatus can also be implemented as, special purpose logic circuitry, e.g., an FPGA (field programmable gate array) or an ASIC (application-specific integrated circuit).

Processors suitable for the execution of a computer program include, by way of example, both general and special purpose microprocessors, and any one or more processors of any kind of digital computer. Generally, a processor will receive instructions and data from a read-only memory or a random access memory or both. The essential elements of a computer are a processor for performing actions in accordance with instructions and one or more memory devices for storing instructions and data. Generally, a computer will also include, or be operatively coupled to receive data from or transfer data to, or both, one or more mass storage devices for storing data, e.g., magnetic, magneto-optical disks, flash memory or optical disks. However, a computer need not have such devices. Moreover, a computer can be embedded in another device, e.g., a mobile telephone, a personal digital assistant (PDA), smart watch, smart glasses, patch, wearable devices, a mobile audio or video player, a game console, a Global Positioning System (GPS) receiver, or a portable storage device (e.g., a universal serial bus (USB) flash drive), to name just a few. Devices suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto-optical disks; and CD-ROM and DVD-ROM disks. The processor and the memory can be supplemented by, or incorporated in, special purpose logic circuitry.

Selected Embodiments

Although the above description and the attached claims disclose a number of embodiments of the present invention, other alternative aspects of the invention are disclosed in the following further embodiments.

Embodiment 1. A system for feeding reinforcement, the system comprising: at least one sensor configured to output physiological data; a sound rendering device; a memory; a control system coupled to the memory, and comprising one or more processors, the control system configured to execute a machine executable code to cause the control system to: receive the physiological data output from the at least one sensor; process, in real-time or near real-time, the physiological data to detect one or more feeding features; and render, in real-time or near real-time, an audio content via the sound rendering device responsive to detecting the one or more feeding features; wherein the one or more feeding features includes a nutritive suck event, a swallow event, and/or a nipple compression event.

Embodiment 2. The system of embodiment 1 wherein the control system is further configured to: responsive to not detecting the one or more feeding features, stop rendering the audio content.

Embodiment 3. The system of embodiment 1, wherein the control system is further configured to: process, in real-time or near real-time, the physiological data to detect a breathing break event; and render, in real-time or near real-time, the audio content responsive to the breathing break event less than a threshold duration; otherwise, stop the rendering audio content.

Embodiment 4. The system of embodiment 1, wherein process the physiological data to detect the one or more feeding features further comprises detect the one or more feeding features according to respective feature thresholds.

Embodiment 5. The system of embodiment 1, wherein render the audio content via the sound rendering device responsive to detecting the one or more feeding features comprises render the audio content in a synchronous manner with the one or more feeding features.

Embodiment 6. The system of embodiment 1, wherein render the audio content via the sound rendering device responsive to detecting the one or more feeding features comprises adjusting one or more parameters of the audio content according to the one or more feeding features, the one or more parameters including a tempo, a volume, a pitch, and/or a meter.

Embodiment 7. The system of embodiment 1, wherein one or more of the at least one sensor and the sound rendering device are disposed within a housing unit, the housing unit removably coupled to a feeding bottle.

Embodiment 8. The system of embodiment 1, wherein the at least one sensor is an audio sensor, an electromyography (EMG) sensor, or a combination sensor including the audio sensor and the EMG sensor.

Embodiment 9. A system for feeding reinforcement, the system comprising: at least one sensor configured to output physiological data; a sound rendering device; a memory; a control system coupled to the memory and comprising one or more processors, the control system configured to execute the machine executable code to cause the control system to: receive, in real-time or near real-time, physiological data output from the at least one sensor; process, in real-time or near real-time, the physiological data to output one or more feeding features; and render, in real-time or near real-time, an audio content via the sound rendering device responsive to detecting a feeding pattern based on the one or more feeding features; otherwise, not render audio content.

Embodiment 10. The system of embodiment 9, wherein the one or more feeding features comprises one or more of a nutritive suck event, a swallow event, a nipple compression event, and a feeding break event.

Embodiment 11. The system of embodiment 10, wherein the control system is further configured to: monitor a duration of the feeding break event; and responsive to the duration less than a threshold duration, continue rendering the audio content; otherwise, stop rendering the audio content.

Embodiment 12. The system of embodiment 10, wherein detecting the feeding pattern based on the one or more feeding features includes detecting an individual rate of occurrence of one or more of the nutritive suck event, the swallow event, and the nipple compression event.

Embodiment 13. The system of embodiment 9, wherein render the audio content via the sound rendering device according to the feeding pattern further comprises adjust one or more parameters of the audio content according to one or more attributes of the feeding pattern, the one or more parameters including a tempo, a volume, a pitch, and/or a meter, and the one or attributes including a frequency, an amplitude, and a duration of the feeding pattern.

Embodiment 14. The system of embodiment 9, wherein the at least one sensor is disposed within a wearable component, the wearable component attachable to a subject.

Embodiment 15. The system of embodiment 9, wherein the at least one sensor is an audio sensor, an electromyography (EMG) sensor, or a combination sensor including the audio sensor and the EMG sensor.

Embodiment 16. A method for feeding reinforcement, comprising: during feeding, receiving, in real-time or near real-time, physiological sensor data from at least one physiological sensor; detecting, in real-time or near real-time, one or more feeding features according to the physiological sensor data, the one or more feeding features including one or more of a nutritive suck event, a swallow event, and a nipple compression event; and rendering, in real-time or near real-time, an audio content responsive to detecting the one or more feeding features.

Embodiment 17. The method of embodiment 16, further comprising: detecting a feeding break according to the physiological data; and not rendering the audio content responsive to the feeding break greater than a threshold break duration.

Embodiment 18. The method of embodiment 16, wherein the one or more feeding features includes a first feeding pattern comprising the nipple compression event followed by the nutritive suck event followed by the swallow event and/or a second feeding pattern comprising the nutritive suck event followed by the swallow event or the nipple compression event followed by the nutritive suck event.

Embodiment 19. The method of embodiment 16, further comprising detecting the nutritive suck event responsive to at least one nutritive suck attribute greater than a nutritive suck attribute threshold; detecting the swallow event responsive to at least one swallow attribute greater than a swallow attribute threshold; and detecting the nipple compression event responsive to at least one nipple compression attribute greater than a nipple compression threshold.

Embodiment 20. The method of embodiment 16, wherein rendering the audio content includes adjusting one or more parameters of the audio content according to a frequency of occurrence of the one or more feeding features, the one or more parameters of the audio content including a tempo, a volume, a pitch, and/or a meter of the audio content.

Embodiment 21. A method for feeding reinforcement, comprising: during a breast-feeding session or a bottle-feeding session, receiving, in real-time or near real-time, physiological sensor data from at least one physiological sensor; detecting, in real-time or near real-time, one or more feeding features according to the physiological sensor data, the one or more feeding features including one or more of a nutritive suck event, a swallow event, and a nipple compression event; and rendering, in real-time or near real-time, an audio content responsive to detecting the one or more feeding features.

Embodiment 22. The method of embodiment 21, further comprising: detecting a feeding break according to the physiological data; and not rendering the audio content responsive to the feeding break greater than a threshold break duration.

Embodiment 23. The method of embodiment 21 wherein the one or more feeding features includes a first feeding pattern comprising the nutritive suck event followed by the swallow event or the nipple compression event followed by the nutritive suck event.

Embodiment 24. The method of embodiment 21, wherein the one or more feeding features includes a second feeding pattern comprising the nipple compression event followed by the nutritive suck event followed by the swallow event.

Embodiment 25. The method of embodiment 21, further comprising detecting the nutritive suck event responsive to at least one nutritive suck attribute greater than a nutritive suck attribute threshold; detecting the swallow event responsive to at least one swallow attribute greater than a swallow attribute threshold; and detecting the nipple compression event responsive to at least one nipple compression attribute greater than a nipple compression threshold.

Embodiment 26. The method of embodiment 21, wherein rendering the audio content includes adjusting one or more parameters of the audio content according to a frequency of occurrence of the one or more feeding features, the one or more parameters of the audio content including a tempo, a volume, a pitch, and/or a meter of the audio content.

Embodiment 27. The method of embodiment 22, wherein the threshold break duration is based on a current feeding pattern.

Embodiment 28. The method of embodiment 22, wherein the threshold break duration is based on an age of an infant undergoing feeding reinforcement.

CONCLUSION

The various methods and techniques described above provide a number of ways to carry out the invention. Of course, it is to be understood that not necessarily all objectives or advantages described can be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as taught or suggested herein. A variety of alternatives are mentioned herein. It is to be understood that some embodiments specifically include one, another, or several features, while others specifically exclude one, another, or several features, while still others mitigate a particular feature by inclusion of one, another, or several advantageous features.

Furthermore, the skilled artisan will recognize the applicability of various features from different embodiments. Similarly, the various elements, features and steps discussed above, as well as other known equivalents for each such element, feature or step, can be employed in various combinations by one of ordinary skill in this art to perform methods in accordance with the principles described herein. Among the various elements, features, and steps some will be specifically included and others specifically excluded in diverse embodiments.

Although the application has been disclosed in the context of certain embodiments and examples, it will be understood by those skilled in the art that the embodiments of the application extend beyond the specifically disclosed embodiments to other alternative embodiments and/or uses and modifications and equivalents thereof.

In some embodiments, the terms "a" and "an" and "the" and similar references used in the context of describing a particular embodiment of the application (especially in the context of certain of the following claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (for example, "such as") provided with respect to certain embodiments herein is intended merely to better illuminate the application and does not pose a limitation on the scope of the application otherwise claimed. No language in the specification should be construed as indicating any non-claimed element essential to the practice of the application.

Certain embodiments of this application are described herein. Variations on those embodiments will become apparent to those of ordinary skill in the art upon reading the foregoing description. It is contemplated that skilled artisans can employ such variations as appropriate, and the application can be practiced otherwise than specifically described herein. Accordingly, many embodiments of this application include all modifications and equivalents of the subject matter recited in the claims appended hereto as permitted by applicable law. Moreover, any combination of the above-described elements in all possible variations thereof is encompassed by the application unless otherwise indicated herein or otherwise clearly contradicted by context.

Particular implementations of the subject matter have been described. Other implementations are within the scope of the following claims. In some cases, the actions recited in the claims can be performed in a different order and still achieve desirable results. In addition, the processes depicted in the accompanying figures do not necessarily require the particular order shown, or sequential order, to achieve desirable results.

All patents, patent applications, publications of patent applications, and other material, such as articles, books, specifications, publications, documents, things, and/or the like, referenced herein are hereby incorporated herein by this reference in their entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that can be employed can be within the scope of the application. Thus, by way of example, but not of limitation, alternative configurations of the embodiments of the application can be utilized in accordance with the teachings herein. Accordingly, embodiments of the present application are not limited to that precisely as shown and described.

The invention claimed is:

1. A system for feeding reinforcement, the system comprising:
    at least one audio sensor configured to output audio data;
    a sound rendering device;
    a housing unit configured to be attached to an exterior of a feeding bottle and having the at least one audio sensor and the sound rendering device disposed therein, the housing unit being a band unit that is configured to extend around the feeding bottle or a cap unit that is configured to receive a bottom of the feeding bottle therein;
    a memory;
    a control system coupled to the memory, and comprising one or more processors, the control system configured to execute a machine executable code to cause the control system to:
        receive the audio data output from the at least one audio sensor;
        process, in real-time or near real-time, the audio data to detect one or more feeding features in the audio data; and
        render, in real-time or near real-time, an audio content via the sound rendering device responsive to detecting the one or more feeding features in the audio data;
        wherein the one or more feeding features are associated with one or more feeding events occurring during a feeding session by an infant, and include a nutritive suck event, a swallow event, and a nipple compression event, or any combination thereof.

2. The system of claim 1, wherein the control system is further configured to, after beginning to render the audio content responsive to detecting the one or more feeding features at a first time, stop rendering the audio content responsive to not detecting any feeding features in the audio data at a second time after the first time.

3. The system of claim 1, wherein the control system is further configured to:

process, in real-time or near real-time, the audio data to detect a feeding break event;
continue to render, in real-time or near real-time, the audio content responsive to a duration of the feeding break event being less than a threshold duration; and
stop the rendering audio content responsive to the duration of the feeding break event being equal to or greater than a threshold duration.

4. The system of claim 1, wherein processing the audio data to detect the one or more feeding features includes:
analyzing the audio data to identify the one or more feeding features within the audio data; and
determining whether each of the one or more identified feeding features satisfies a respective performance threshold, the respective performance threshold of each respective feeding feature being associated with a desired value of an attribute of the respective feeding feature.

5. The system of claim 1, wherein rendering the audio content via the sound rendering device responsive to detecting the one or more feeding features in the audio data comprises adjusting one or more parameters of the audio content to match a current frequency of the one or more feeding features or a desired frequency of the one or more feeding features.

6. The system of claim 1, wherein rendering the audio content via the sound rendering device responsive to detecting the one or more feeding features in the audio data comprises adjusting one or more parameters of the audio content according to the one or more feeding features, the one or more parameters including a tempo, a volume, a pitch, a meter, or any combination thereof.

7. The system of claim 1, wherein processing the audio data to detect the one or more feeding features in the audio data includes inputting at least a portion of the audio data into a machine learning algorithm that is trained to detect the one or more feeding features.

8. The system of claim 3, wherein rendering the audio content responsive to detecting the one or more feeding features includes:
rendering the audio content responsive to the one or more detected feeding features satisfying the respective performance threshold; and
not rendering the audio content responsive to the one or more detected feeding features not satisfying the respective performance threshold.

9. The system of claim 4, wherein the desired characteristic of the respective feeding feature includes a desired amplitude, a desired frequency, a desired duration, or any combination thereof.

10. A system for feeding reinforcement, the system comprising:
at least one audio sensor configured to output audio data;
a sound rendering device;
a housing unit configured to be attached to an exterior of a feeding bottle and having the at least one audio sensor and the sound rendering device disposed therein, the housing unit being a band unit that is configured to extend around the feeding bottle or a cap unit that is configured to receive a bottom of the feeding bottle therein;
a memory;
a control system coupled to the memory and comprising one or more processors, the control system configured to execute the machine executable code to cause the control system to:
receive the audio data output from the at least one audio sensor;
process, in real-time or near real-time, the audio data to detect one or more feeding features in the audio data, each feeding feature being associated with a respective feeding event;
identifying a feeding pattern based on the one or more feeding features, the feeding pattern including at least two different feeding events; and
render, in real-time or near real-time, audio content via the sound rendering device responsive to identifying the feeding pattern.

11. The system of claim 10, wherein the respective feeding event associated with each of the one or more feeding features include a nutritive suck event, a swallow event, a nipple compression event, a feeding break event, or any combination thereof.

12. The system of claim 11, wherein after beginning to render the audio content, the control system is further configured to:
monitor a duration of the feeding break event;
responsive to the duration of the feeding break event being less than a threshold duration, continue rendering the audio content; and
responsive to the duration being equal to or greater than the threshold duration, stop rendering the audio content.

13. The system of claim 11, wherein the feeding pattern includes a rate of occurrence of a plurality of nutritive suck events, a plurality of swallow events, or a plurality of nipple compression events satisfying a threshold.

14. The system of claim 11, wherein the feeding pattern includes an occurrence of the nutritive suck event or the nipple compression event, and an occurrence of the swallow event within a threshold window of time following the occurrence of the nutritive suck event or the nipple compression event.

15. The system of claim 11, wherein the feeding pattern includes an occurrence of the nipple compression event, an occurrence of the nutritive suck within a first threshold window of time following the occurrence of the nipple compression event, and an occurrence of the swallow event within a second threshold window of time following the occurrence of the nutritive suck event.

16. The system of claim 10, wherein rendering the audio content via the sound rendering device responsive to identifying the feeding pattern include adjusting one or more parameters of the audio content according to one or more attributes of the feeding pattern, the one or more parameters of the audio content including a tempo, a volume, a pitch, a meter, or any combination thereof, and the one or more attributes of the feeding pattern including a frequency of the feeding pattern, an amplitude of the feeding pattern, a duration of the feeding pattern, or any combination thereof.

17. The system of claim 10, wherein the at least one audio sensor is disposed within a wearable component, the wearable component attachable to a subject.

18. A method for feeding reinforcement, comprising:
during feeding,
receiving, in real-time or near real-time, audio data from at least one audio sensor;
detecting, in real-time or near real-time, one or more feeding features according to the physiological sensor data, the one or more feeding features associated with one or more feeding events that include a nutritive suck event, a swallow event, a nipple compression event, or any combination thereof; and rendering, in real-time or near real-time, an audio content responsive to detecting the one or more feeding features, wherein the at least one audio sensor and the sound rendering device are disposed within a housing unit that is configured to be attached to an exterior of a feeding bottle, the housing unit being a band unit configured to extend around the feeding bottle or a cap unit that is configured to receive a bottom of the feeding bottle therein.

19. The method of claim 18, further comprising:

detecting a feeding break event based on the audio data;

continuing to render the audio content responsive to a duration of the feeding break event being less than a threshold duration; and not rendering the audio content responsive to the duration of the feeding break being greater than or equal to the threshold duration.

20. The method of claim 18, further comprising identifying a feeding pattern based on the one or more feeding features, the identified feeding pattern including a first feeding pattern that includes an occurrence of the nipple compression event followed by an occurrence of the nutritive suck event followed by an occurrence of the swallow event, a second feeding pattern that includes an occurrence of the nutritive suck event or the nipple compression event followed by an occurrence of the nutritive suck event, wherein the audio content is rendered responsive to identifying the first feeding pattern, the second feeding pattern, or both.

21. The method of claim 18, wherein detecting the one or more feeding features includes (i) identifying the nutritive suck event and confirming that at least one nutritive suck attribute is greater than a nutritive suck attribute threshold, (ii) identifying the swallow event and confirming that at least one swallow attribute greater than a swallow attribute threshold, (iii) identifying the nipple compression event and confirming that at least one nipple compression attribute greater than a nipple compression threshold, or (iv) any combination of (i)-(iii).

22. The method of claim 18, wherein rendering the audio content includes adjusting one or more parameters of the audio content according to a frequency of occurrence of the one or more feeding features, the one or more parameters of the audio content including a tempo, a volume, a pitch, a meter, or any combination thereof.

* * * * *